United States Patent [19]
Phillips et al.

[11] Patent Number: 6,110,914
[45] Date of Patent: Aug. 29, 2000

[54] SPIROAZABICYCLIC HETEROCYCLIC COMPOUNDS

[75] Inventors: Eifion Phillips, West Henrietta; Robert Mack, Rochester, both of N.Y.; John Macor, Flemington, N.J.; Simon Semus, Bensalem, Pa.

[73] Assignee: Astra Aktiebolag, Sodertalje, Sweden

[21] Appl. No.: 09/171,983

[22] PCT Filed: Jul. 10, 1998

[86] PCT No.: PCT/SE98/01364

§ 371 Date: Oct. 29, 1998

§ 102(e) Date: Oct. 29, 1998

[87] PCT Pub. No.: WO99/03859

PCT Pub. Date: Jan. 28, 1999

[30] Foreign Application Priority Data

Jul. 18, 1997 [SE] Sweden .................................. 9702746
Mar. 24, 1998 [SE] Sweden .................................. 9800977

[51] Int. Cl.[7] ....................... A61K 31/5377; A61P 25/28; C07P 499/21
[52] U.S. Cl. .......................... 514/233.2; 544/70; 544/230; 546/14; 546/18; 540/543
[58] Field of Search .................. 544/70; 546/18; 514/233.2

[56] References Cited

U.S. PATENT DOCUMENTS 3,681,363 8/1972 Elkin et al. ............................... 546/18
5,468,875 11/1995 Saab et al. .

FOREIGN PATENT DOCUMENTS

96/06098 2/1996 WIPO .
97/05139 2/1997 WIPO .

OTHER PUBLICATIONS

Pharmazie 48, pp. 465–466 (1993), H. 6.
Nilsson et al, "Studies on carbanilic acid esters of cyclic amino alcohols," Acta Pham. Succica 7, pp. 239–246 (1970).
McDonald et al, "Chaper 5. Nicotinic Acetylcholine Receptors: Molecular...,"Annual Reports in Medicinal Chemistry 30, pp. 41–50 (1995).
Williams et al, "Neuronal Nicotinic Actylcholine Receptors, "DN&P, vol. 7, No. 4, pp. 206–222 (1994).
Nordvall et al, "3–(2–Benzofuranyl)quinuclidin–2ene Derivatives . . . ,"J. Med. Chem., Voo. 39, pp. 3269–3277 (1996).
[Isp7].

Primary Examiner—Robert W. Ramsuer
Attorney, Agent, or Firm—Nixon & Vanderhye

[57] ABSTRACT

A compound of formula

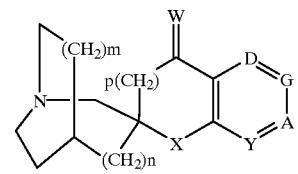

wherein n is 0 or 1; m is 0 or 1; p is 0 or 1; X is oxygen or sulfur; Y is CH, N or NO; W is oxygen, $H_2$ or $F_2$;

A is N or $C(R^2)$; G is N or $C(R^3)$; D is N or $C(R^4)$;
with the proviso that no more than one of A, G, and D is nitrogen, but at least one of Y, A, G, and D is nitrogen or NO;
$R^1$ is hydrogen or $C_1$ to $C_4$ alkyl;
$R^2$, $R^3$, and $R^4$ are independently hydrogen, halogen, $C_1$–$C_4$ alkyl, $C_2$–$C_4$ alkenyl, $C_2$–$C_4$ alkynyl, aryl, heteroaryl, OH, $OC_1$–$C_4$ alkyl, $CO_2R^1$, —CN, —$NO_2$, —$NR^5R^6$, —$CF_3$, —$OSO_2CF_3$ or $R^2$ and $R^3$, or $R^3$ and $R^4$, respectively, may together form another six membered aromatic or heteroaromatic ring sharing A and G, or G and D, respectively, containing between zero and two nitrogen atoms, and substituted with one to two of the following substituents: independently hydrogen, halogen, $C_1$–$C_4$ alkyl, $C_2$–$C_4$ alkenyl, $C_2$–$C_4$ alkynyl, aryl, heteroaryl, OH, $OC_1$–$C_4$ alkyl, $CO_2R^1$, —CN, —$NO_2$, —$NR^5R^6$, —$CF_3$, —$OSO_2CF_3$; $R^5$ and $R^6$ are independently hydrogen, $C_1$–$C_4$ alkyl, $C(O)R^7$, $C(O)NHR^8$, $C(O)OR^9$, $SO_2R^{10}$ or may together be $(CH_2)_jQ(CH_2)_k$ where Q is O, S, $NR^{11}$, or a bond; j is 2 to 7, k is 0 to 2; $R^7$, $R^8$, $R^9$, $R^{10}$, and $R^{11}$ are independently $C_1$–$C_4$ alkyl, aryl, or heteroaryl, or an enantiomer thereof, and the pharmaceutically acceptable salts thereof, processes for preparing them, composition containing them, and their use in therapy, especially in the treatment or prophylaxis of psychotic disorders and intellectual impairment disorders.

23 Claims, No Drawings

SPIROAZABICYCLIC HETEROCYCLIC COMPOUNDS

This application is a 371 of PCT/SE 98/01364 filed Jul. 10, 1998.

TECHNICAL FIELD

This invention relates to novel spiroazabicyclic heterocyclic amines or pharmaceutically acceptable salts thereof, processes for preparing them, pharmaceutical compositions containing them and their use in therapy. A further object is to provide active compounds which are potent ligands for nicotinic acetylcholine receptors (nAChR's).

BACKGROUND OF THE INVENTION

The use of compounds which bind nicotinic acetylcholine receptors in the treatment of a range of disorders involving reduced cholinergic function such as Alzheimer's disease, cognitive or attention disorders, anxiety, depression, smoking cessation, neuroprotection, schizophrenia, analgesia, Tourette's syndrome, and Parkinson's disease has been discussed in McDonald et al. (1995) "Nicotinic Acetylcholine Receptors: Molecular Biology, Chemistry and Pharmacology", Chapter 5 in Annual Reports in Medicinal Chemistry, vol. 30, pp. 41–50, Academic Press Inc., San Diego, Calif.; and in Williams et al. (1994) "Neuronal Nicotinic Acetylcholine Receptors," Drug News & Perspectives, vol. 7, pp. 205–223.

U.S. Pat. No. 5,468,875 discloses N-alkylcarbamic acid 1-azabicyclo[2.2.1]hept-3-yl esters which are centrally active muscarinic agents useful in the treatment of Alzheimer's disease and other disorders.

N-(2-alkoxyphenyl)carbamic acid 1-azabicyclo[2.2.2] octan-3-yl esters are disclosed in Pharmazie, vol. 48, 465–466 (1993) along with their local anesthetic activity. N-phenylcarbamic acid 1-azabicyclo[2.2.2]octan-3-yl esters substituted at the ortho position on the phenyl ring are described as local anaesthetics in *Acta Pharm. Suecica*, 7, 239–246 (1970).

Furopyridines useful in controlling synaptic transmission are disclosed in WO 97/05139.

DISCLOSURE OF THE INVENTION

According to the invention it has been found that a compound of formula I

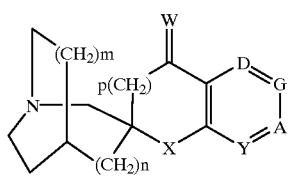

I wherein n is 0 or 1;
m is 0 or 1;
p is 0 or 1;
Y is CH, N or NO
X is oxygen or sulfur;
W is oxygen, $H_2$ or $F_2$;
A is N or $C(R^2)$
G is N or $C(R^3)$;
D is N or $C(R^4)$;

with the proviso that no more than one of A, G, and D is nitrogen but at least one of Y, A, G, and D is nitrogen or NO;

$R^1$ is hydrogen or $C_1$–$C_4$ alkyl;

$R^2$, $R^3$, and $R^4$ are independently hydrogen, halogen, $C_1$–$C_4$ alkyl, $C_2$–$C_4$ alkenyl, $C_2$–$C_4$ alkynyl, aryl, heteroaryl, OH, $OC_1$–$C_4$ alkyl, $CO_2R^1$, —CN, —$NO_2$, —$NR^5R^6$, —$CF_3$, —$OSO_2CF_3$, or $R^2$ and $R^3$, or $R^3$ and $R^4$, respectively, may together form another six membered aromatic or heteroaromatic ring sharing A and G, or G and D, respectively containing between zero and two nitrogen atoms, and substituted with one to two of the following substituents: independently hydrogen, halogen, $C_1$–$C_4$ alkyl, $C_2$–$C_4$ alkenyl, $C_2$–$C_4$ alkynyl, aryl, heteroaryl, OH, $OC_1$–$C_4$ alkyl, $CO_2R^1$, —CN, —$NO_2$, —$NR^5R^6$, —$CF_3$, $OSO_2CF_3$;

$R^5$ and $R^6$ are independently hydrogen, $C_1$–$C_4$ alkyl, $C(O)R^7$, $C(O)NHR^8$, $C(O)OR^9$, $SO_2R^{10}$ or may together be $(CH_2)_jQ(CH_2)_k$ where Q is O, S, $NR^{11}$, or a bond;

j is 2 to 7;

k is 0 to 2;

$R^7$, $R^8$, $R^9$, $R^{10}$, and $R^{11}$ are independently $C_1$–$C_4$ alkyl, aryl, or heteroaryl, or an enantiomer thereof, and the pharmaceutically acceptable salts thereof is a potent ligand for nicotinic acetylcholine receptors.

Unless otherwise indicated, the $C_1$–$C_4$ alkyl groups referred to herein, e.g., methyl, ethyl, n-propyl, n-butyl, i-propyl, i-butyl, t-butyl, s-butyl, may be straight-chained or branched, and the $C_3$–$C_4$ alkyl groups may also be cyclic, e.g., cyclopropyl,cyclobutyl.

Unless otherwise indicated, the $C_1$–$C_6$ alkyl groups referred to herein, e.g., methyl, ethyl, n-propyl, n-butyl, i-propyl, i-butyl, t-butyl, s-butyl, n-pentyl, i-pentyl, t-pentyl, neo-pentyl, n-hexyl, or i-hexyl may be straight-chained or branched, and the $C_3$–$C_6$ alkyl groups may also be cyclic, e.g., cyclopropyl, cyclobutyl, cyclopentyl or cyclohexyl.

Unless otherwise indicated, the $C_1$–$C_4$ alkoxy groups referred to herein, e.g., methoxy, ethoxy, n-propoxy, i-propoxy, n-butoxy, i-butoxy, t-butoxy, s-butoxy, may be straight-chained or branched.

Unless otherwise indicated, the $C_2$–$C_4$ alkenyl groups referred to herein may contain one or two double bonds, e.g., ethenyl, i-propenyl, n-butenyl, i-butenyl, allyl, 1,3-butadienyl.

Unless otherwise indicated, the $C_2$–$C_4$ alkynyl groups referred to herein contain one triple bond, e.g., ethynyl, propynyl, 1- or 2-butynyl.

Halogen referred to herein may be fluoride, chloride, bromide, or iodide.

Unless otherwise indicated, aryl refers to a phenyl ring optionally substituted with one to three of the following substituents: hydrogen, halogen, $C_1$–$C_4$ alkyl, $C_2$–$C_4$ alkenyl, $C_2$–$C_4$ alkynyl, OH, $OC_1$–$C_4$ alkyl, $CO_2R^1$, —CN, —$NO_2$, —$NR^5R^6$, —$CF_3$;

Unless otherwise indicated, heteroaryl refers to a five- or six-membered aromatic ring containing one or two nitrogen atoms, such as pyridyl, pyrazinyl, pyrimidinyl, pyridazinyl, pyrrolyl, imidazolyl or pyrazolyl, with the carbon atoms of that ring optionally substituted with one to three of the following substituents: hydrogen, halogen, $C_1$–$C_4$ alkyl, $C_2$–$C_4$ alkenyl, $C_2$–$C_4$ alkynyl, OH, $OC_1$–$C_4$ alkyl, $CO_2R^1$, —CN, —$NO_2$, —$NR^5R^6$, —$CF_3$; $R^5$ and $R^6$ may together be $(CH_2)_jQ(CH_2)_k$ where Q is O, S, $NR^{11}$, or a bond, and where j is 2 to 7, preferably 2 to 3, and k is 0 to 2, so as to form a 3–7 membered ring, preferably a 5- or 6-membered ring, for example pyrrolidinyl, imidazolidinyl piperazinyl, piperidyl, morpholinyl, or thiomorpholinyl.

$R^2$ and $R^3$ may together form another six membered aromatic or heteroaromatic ring sharing A and G containing between zero and two nitrogen atoms refers to groups such as quinoline, 1,5-, 1,6-, 1,7-, or 1,8-diazanaphthalene.

$R^3$ and $R^4$ may together form another six membered aromatic or heteroaromatic ring sharing G and D containing between zero and two nitrogen atoms refers to groups such as isoquinoline, 2,5-, 2,6-, 2,7-, or 2,8-diazanaphthalene.

Preferred compounds of the invention are compounds of formula I wherein m is 1; n is 0; p is 0; X is oxygen; W is $H_2$; A is $C(R^2)$; G is $C(R^3)$; D is $C(R^4)$.

Preferred compounds of the invention include the following:

spiro[1-azabicyclo[2.2.2]octane-3,2'-(3'H)-furo[2,3-b]pyridine];

5'-bromospiro[1-azabicyclo[2.2.2]octane-3,2'-(3'H)-furo[2,3-b]pyridine];

5'-phenylspiro[1-azabicyclo[2.2.2]octane-3,2'-(3'H)-furo[2,3-b]pyridine];

5'-nitrospiro[1-azabicyclo[2.2.2]octane-3,2'-(3'H)-furo[2,3-b]pyridine];

1'-chlorospiro[1-azabicyclo[2.2.2]octane-3,2'-(3'H)-furo[2,3-b]isoquinoline];

5'-(phenylcarboxamido)spiro[1-azabicyclo[2.2.2]octane-3,2'-(3'H)-furo[2,3-b ]pyridine];

5'-(phenylaminocarbonylamino)spiro[1-azabicyclo[2.2.2]octane-3,2'-(3'H)-furo[2,3-b]pyridine];

5'-(phenylsulfonylamido)spiro[1-azabicyclo[2.2.2]octane-3,2'-(3'H)-furo[2,3-b ]pyridine];

5'-aminospiro[1-azabicyclo[2.2.2]octane-3,2'-(3'H)-furo[2,3-b]pyridine];

5'-N-methylaminospiro[1-azabicyclo[2.2.2]octane-3,2'-(3'H)-furo[2,3-b]pyridine];

5'-N,N-dimethylaminospiro[1-azabicyclo[2.2.2]octane-3,2'-(3'H)-furo[2,3b]pyridine];

5'-N,N-diethylaminospiro[1-azabicyclo[2.2.2]octane-3,2'-(3'H)-furo[2,3-b]pyridine];

5'-N-ethylaminospiro[1-azabicyclo[2.2.2]octane-3,2'-(3'H)-furo[2,3-b]pyridine];

5'-N-benzylaminospiro[1-azabicyclo[2.2.2]octane-3,2'-(3'H)-furo[2,3-b]pyridine];

5'-N-formamidospiro[1-azabicyclo[2.2.2]octane-3,2'-(3'H)-furo[2,3-b]pyridine];

5'-N-acetamidospiro[1-azabicyclo[2.2.2]octane-3,2'-(3'H)-furo[2,3-b]pyridine];

spiro[1-azabicyclo[2.2.2]octane-3,2'-(3'H)-furo[2,3-b]isoquinoline];

spiro[1-azabicyclo[2.2.2]octane-3,2'-(3'H)-furo[2,3-b]quinoline];

5'-ethenylspiro[1-azabicyclo[2.2.2]octane-3,2'-(3'H)-furo[2,3-b]pyridine];

5'-(E)-(phenylethenyl)spiro[1-azabicyclo[2.2.2]octane-3,2'-(3'H)-furo[2,3-b]pyridine];

5'-(4-morpholino)spiro[1-azabicyclo[2.2.2]octane-3,2'-(3'H)-furo[2,3-b]pyridine];

5'-(1-azetidinyl)spiro[1-azabicyclo[2.2.2]octane-3,2'-(3'H)-furo[2,3-b]pyridine];

5'-(E)-(2-(4-pyridyl)ethenyl)spiro[1-azabicyclo[2.2.2]octane-3,2'-(3'H)-furo[2,3-b]pyridine];

5'-(E)-(2-(2-pyridyl)ethenyl)spiro[1-azabicyclo[2.2.2]octane-3,2'-(3'H)-furo[2,3-b]-pyridine];

5'-(2-trimethylsilylethynyl)spiro[1-azabicyclo[2.2.2]octane-3,2'-(3'H)-furo[2,3-b]pyridine];

5'-ethynylspiro[1-azabicyclo[2.2.2]octane-3,2'-(3'H)-furo[2,3-b]pyridine];

5'-(2-furyl)spiro[1-azabicyclo[2.2.2]octane-3,2'-(3'H)-furo[2,3-b]pyridine];

5'-(3-pyridyl)spiro[1-azabicyclo[2.2.2]octane-3,2'-(3'H)-furo[2,3-b]pyridine];

5'-methylspiro[1-azabicyclo[2.2.2]octane-3,2'-(3'H)-furo[2,3-b]pyridine];

spiro[1-azabicyclo[2.2.2]octane-3,2'-(3'H)-furo[2,3-b]pyridine-5'carbonitrile];

spiro[1-azabicyclo[2.2.2]octane-3,2'-(3'H)-furo[2,3-b]pyridine-5'carboxamide];

5'-N'-(3-chlorophenyl)aminocarbonylminospiro[1-azabicyclo[2.2.2]octane-3,2'-(3'H)-furo[2,3-b]pyridine];

5'-N'-(2-nitrophenyl)aminocarbonylaminospiro[1-azabicyclo[2.2.2]octane-3,2'-(3'H)-furo[2,3-b]pyridine];

4'-chlorospiro[1-azabicyclo[2.2.2]octane-3,2'-(3'H)-furo[2,3-b]pyridine];

4'-methoxyspiro[1-azabicyclo[2.2.2]octane-3,2'-(3'H)-furo[2,3-b]pyridine];

4'-phenylthiospiro[1-azabicyclo[2.2.2]octane-3,2'-(3'H)-furo[2,3-b]pyridine];

4'-(N-2-aminoethyl)aminospiro[1-azabicyclo[2.2.2]octane-3,2'-(3'H)-furo[2,3-b]pyridine];

4'-phenylaminospiro[1-azabicyclo[2.2.2]octane-3,2'-(3'H)-furo[2,3-b]pyridine];

4'-methylaminospiro[1-azabicyclo[2.2.2]octane-3,2'-(3'H)-furo[2,3-b]pyridine];

4'-(4-N-methylpiperazin-1-yl)spiro[1-azabicyclo[2.2.2]octane-3,2'-(3'H)-furo[2,3-b]pyridine];

4'-chloro-spiro[1-azabicyclo[2.2.2]octane-3,2'-(3'H)-furo[3,2-c]pyridine];

spiro[1-azabicyclo[2.2.2]octane-3,2'-(3'H)-furo[3,2-c]pyridine];

spiro[1-azabicyclo[2.2.2]octane-3,2'(3'H)-furo[2,3-b]pyridine-7'-oxide];

spiro[1-azabicyclo[2.2.2]octane-3,2'(3'H)-furo[2,3-b]pyridine-6'-carbonitrile];

6'-chlorospiro[1-azabicyclo[2.2.2]octane-3,2'(3'H)-furo[2,3-b]pyridine];

6'-fluorospiro[1-azabicyclo[2.2.2]octane-3,2'(3'H)-furo[2,3-b]pyridine]; and the enantiomers, and pharmaceutically acceptable salts thereof.

Particularly preferred compounds of the invention are compounds of formula I wherein m is 1; n is 0; p is 0; X=oxygen; W is $H_2$; A=CH, D=CH, and G=C(R3), including the following compounds:

spiro[1-azabicyclo[2.2.2]octane-3,2'-(3'H)-furo[2,3-b]pyridine];

spiro[1-azabicyclo[2.2.2]octane-3,2'(3'H)-furo[2,3-b]pyridine-7'-oxide];

5'-bromospiro[1-azabicyclo[2.2.2]octane-3,2'-(3'H)-furo[2,3-b]pyridine];

5'-phenylspiro[1-azabicyclo[2.2.2]octane-3,2'-(3'H)-furo[2,3-b]pyridine];

5'-nitrospiro[1-azabicyclo[2.2.2]octane-3,2'-(3'H)-furo[2,3-b]pyridine];

5'-(phenylcarboxamido)spiro[1-azabicyclo[2.2.2]octane-3,2'-(3'H)-furo[2,3-b]pyridine];

5'-(phenylaminocarbonylamino)spiro[1-azabicyclo[2.2.2]octane-3,2'-(3'H)-furo[2,3-b]pyridine];

5'-(phenylsulfonylamido)spiro[1-azabicyclo[2.2.2]octane-3,2'-(3'H)-furo[2,3-b]pyridine];

5'-aminospiro[1-azabicyclo[2.2.2]octane-3,2'-(3'H)-furo[2,3-b]pyridine];

5'-N-methylaminospiro[1-azabicyclo[2.2.2]octane-3,2'-(3'H)-furo[2,3-b]pyridine];

5'-N,N-dimethylaminospiro[1-azabicyclo[2.2.2]octane-3,2'-(3'H)-furo[2,3-b]pyridine];
5'-N,N-diethylaminospiro[1-azabicyclo[2.2.2]octane-3,2'-(3'H)-furo[2,3-b]pyridine];
5'-N-ethylaminospiro[1-azabicyclo[2.2.2]octane-3,2'-(3'H)-furo[2,3-b]pyridine];
5'-N-benzylaminospiro[1-azabicyclo[2.2.2]octane-3,2'-(3'H)-furo[2,3-b]pyridine];
5'-N-formamidospiro[1-azabicyclo[2.2.2]octane-3,2'-(3'H)-furo[2,3-b]pyridine];
5'-N-acetamidospiro[1-azabicyclo[2.2.2]octane-3,2'-(3'H)-furo[2,3-b]pyridine];
5'-ethenylspiro[1-azabicyclo[2.2.2]octane-3,2'-(3'H)-furo[2,3-b]pyridine];
5'-(E)-(phenylethenyl)spiro[1-azabicyclo[2.2.2]octane-3,2'-(3'H)-furo[2,3-b]pyridine];
5'-(4-morpholino)spiro[1-azabicyclo[2.2.2]octane-3,2'-(3'H)-furo[2,3-b]pyridine];
5'-(1-azetidinyl)spiro[1-azabicyclo[2.2.2]octane-3,2'-(3'H)-furo[2,3-b]pyridine];
5'-(E)-(2-(4-pyridyl)ethenyl)spiro[1-azabicyclo[2.2.2]octane-3,2'-(3'H)-furo[2,3-b]pyridine];
5'-(E)-(2-(2-pyridyl)ethenyl)spiro[1-azabicyclo[2.2.2]octane-3,2'-(3'H)-furo[2,3-b]pyridine];
5'-(2-trimethylsilylethynyl)spiro[1-azabicyclo[2.2.2]octane-3,2'-(3'H)-furo[2,3-b]pyridine];
5'-ethynylspiro[1-azabicyclo[2.2.2]octane-3,2'-(3'H)-furo[2,3-b]pyridine];
5'-(2-furyl)spiro[1-azabicyclo[2.2.2]octane-3,2'-(3'H)-furo[2,3-b]pyridine];
5'-(3-pyridyl)spiro[1-azabicyclo[2.2.2]octane-3,2'-(3'H)-furo[2,3-b]pyridine];
5'-methylspiro[1-azabicyclo[2.2.2]octane-3,2'-(3'H)-furo[2,3-b]pyridine];
spiro[1-azabicyclo[2.2.2]octane-3,2'-(3'H)-furo[2,3-b]pyridine-5'carbonitrile];
spiro[1-azabicyclo[2.2.2]octane-3,2'-(3'H)-furo[2,3-b]pyridine-5'carboxamide];
5'-N'-(3-chlorophenyl)aminocarbonylminospiro[1-azabicyclo[2.2.2]octane-3,2'-(3'H)-furo[2,3-b]pyridine];
5'-N'-(2-nitrophenyl)aminocarbonylaminospiro[1-azabicyclo[2.2.2]octane-3,2'-(3'H)-furo[2,3-b]pyridine];

Methods of Preparation

In the reaction schemes and text that follow, A, G, D, X, W, Y, Z, m, n, and p, unless otherwise indicated, are as defined above for formula I.

(A) Compounds wherein p is 0 and Y is N

The compounds of formula I, wherein p is 0 and Y is N, may be prepared according to the methods outlined in Scheme I.

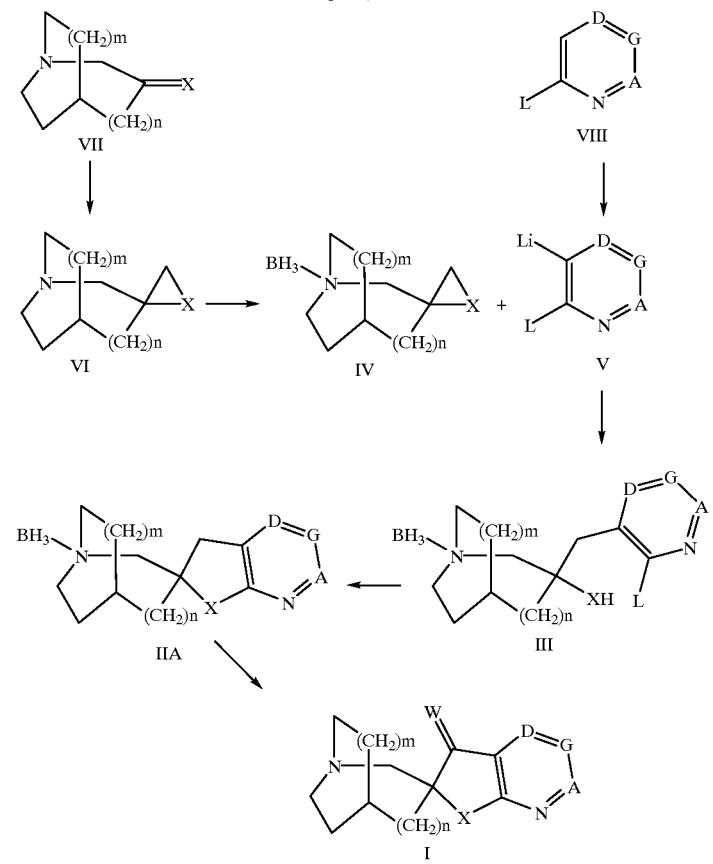

Compounds of formula I where W=$H_2$ and p is 0 may be prepared from the deprotection of a compound of formula IIA using acid in a suitable solvent. Suitable acids include mineral, organic and Lewis acids, for example, hydrochloric and hydrobromic acid, sulfuric acid, triflic acid, methanesulfonic acid, and boron trifluoride etherate. The preferred acid is hydrobromic acid. Suitable solvents include acetone, butanone, ethanone, and pinacolone. The preferred solvent is acetone. The reaction is usually conducted at a temperature from about −10° C. to about 100° C., preferably about 0° C. to about 60° C. Alternatively the deprotection may be conducted by heating the borane complex in alcoholic solvents. A preferred method is by refluxing a ethanolic solution of the complex.

Compounds of formula I where W=O (oxygen) and p is 0 may be prepared by the oxidation of compounds of formula IIA, for example using selenium dioxide, or by reaction first with N-bromosuccinimide then with sodium bicarbonate and methylsulfoxide, followed by removal of the borane group as described above.

Compounds of formula I where W=F$_2$ and p is 0 may be prepared from compounds of formula I where W=O by reaction with a fluorinating agent, for example diethylaminosulfur trifluoride.

Compounds of formula IIA may be prepared from the cyclization of a compound of formula III wherein L is fluoro, chloro, bromo, iodo, —OCH$_3$, —SPh, —SCH$_3$, —SO$_2$Ph, or —SO$_2$CH$_3$ in the presence of a base in an inert solvent. Suitable bases include sodium hydride, sodium amide, potassium hydride, potassium t-amylate, potassium t-butoxide, and potassium bis(trimethylsilyl)amide. The preferred base is sodium hydride. Suitable inert solvents include N,N-dimethylformamide, N-methylpyrrolidin-2-one, ethers such as diethyl ether, tetrahydrofuran, and 1,4-dioxane, and dimethylsulfoxide. The preferred inert solvent is N,N-dimethylformamide. The reaction is usually conducted at a temperature from about 10° C. to about 100° C., preferably about 20° C. to about 66° C.

Compounds of formula III wherein L is fluoro, chloro, bromo, iodo, —OCH$_3$, —SPh, —SCH$_3$, —SO$_2$Ph, or —SO$_2$CH$_3$ may be prepared by the reaction of a compound of formula IV with a compound of formula V wherein L is defined as above in an inert solvent. Suitable inert solvents include diethyl ether, tetrahydrofuran and 1,4-dioxane. The preferred inert solvent is tetrahydrofuran. The reaction is usually conducted at a temperature from about −100° C. to about 0° C., preferably about −78° C. to about −25° C.

Compounds of formula V wherein L is defined as above may be prepared from a compound of formula VIII wherein L is defined as above using a lithium base and a proton transfer agent in an inert solvent. Suitable lithium bases include lithium diisopropylamide, n-butyllithium, sec-butyllithium, tert-butyllithium, and phenyllithium. The preferred lithium base is phenyllithium. Suitable proton transfer agents include hindered secondary amines such as diisopropylamine and 2,2,6,6-tetramethylpiperidine. The preferred proton transfer agent is diisopropylamine. Suitable inert solvents include diethyl ether, tetrahydrofuran and 1,4-dioxane. The preferred inert solvent is tetrahydrofuran. The reaction is usually conducted at a temperature from about −100° C. to about 0° C., preferably about −78° C. to about −25° C. Compounds of formula V are usually taken directly into the reaction with compounds of formula IV without purification.

Compounds of formula IV may be prepared from the reaction of a compound of formula VI with borane (BH$_3$ or B$_2$H$_6$) in an inert solvent. Borane in tetrahydrofuran is preferred. Suitable inert solvents include diethyl ether, tetrahydrofuran and 1,4-dioxane. The preferred inert solvent is tetrahydrofuran. The reaction is usually conducted at a temperature from about −10° C. to about 66° C., preferably about 0° C. to about 20° C.

Compounds of formula VIII are known, e.g., either commercially available or may be prepared by methods known to one skilled in the art (see e.g, The Chemistry of Heterocyclic Compounds, Pyridine and Its Derivatives, Part 1, E. Klingsberg, Ed., Interscience Publishers, Inc, NY, 1960).

Compounds of formula VI may be prepared from compounds of formula VII by methods known to one skilled in the art. For example, compounds of formula VI wherein X represents oxygen may be prepared from the corresponding compound of formula VII wherein X represents the oxygen of a ketone using one of the reagents well known in the art for preparation of oxiranes from ketones (see e.g. the reactions referenced in J. March, "Advanced Organic Chemistry" (1985) 3rd Edition, page 1161). Compounds of formula VI wherein X represents sulfur may be prepared from the corresponding compound of formula VII wherein X represents either oxygen or sulfur using one of the methods well known in the art for preparation of episulfides from ketones or thioketones (see, e.g. the reactions referenced in J. March, "Advanced Organic Chemistry" (1985) 3rd Edition, pages 866–867).

Compounds of formula VII are known, e.g., either commercially available or may be prepared by methods known to one skilled in the art (see, e.g, The Chemistry of Heterocyclic Compounds, Heterocyclic Systems with Bridgehead Nitrogen Atoms, Part 2, W. L. Mosby, Ed., Interscience Publishers, Inc, NY, 1961).

(B) Compounds wherein p is 1 and Y is N

The compounds of formula I (p=1) may be prepared according to the methods described in Scheme II or Scheme III, below.

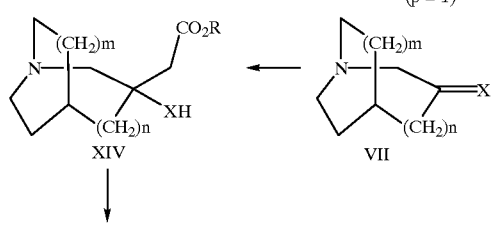

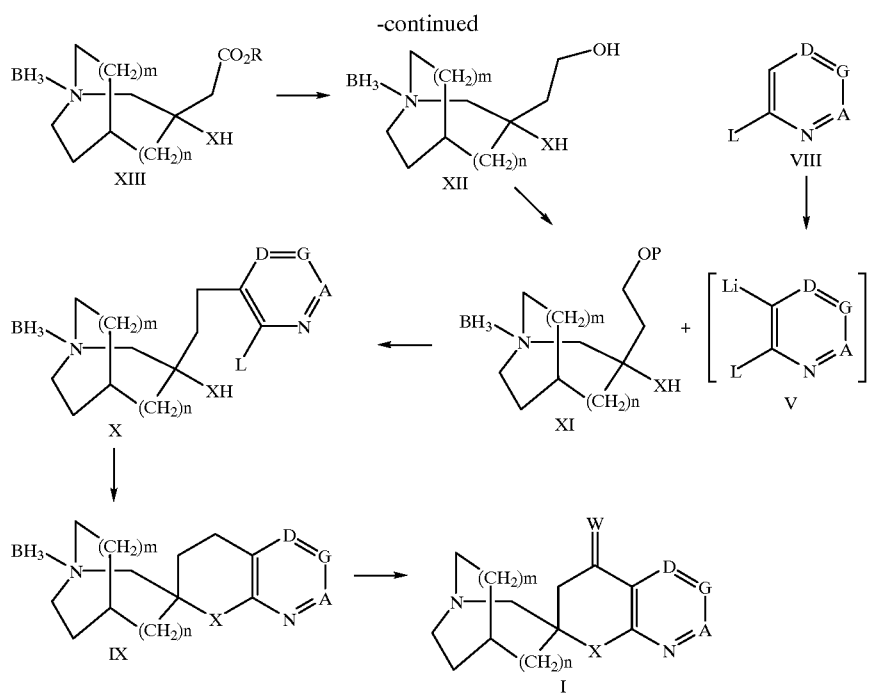

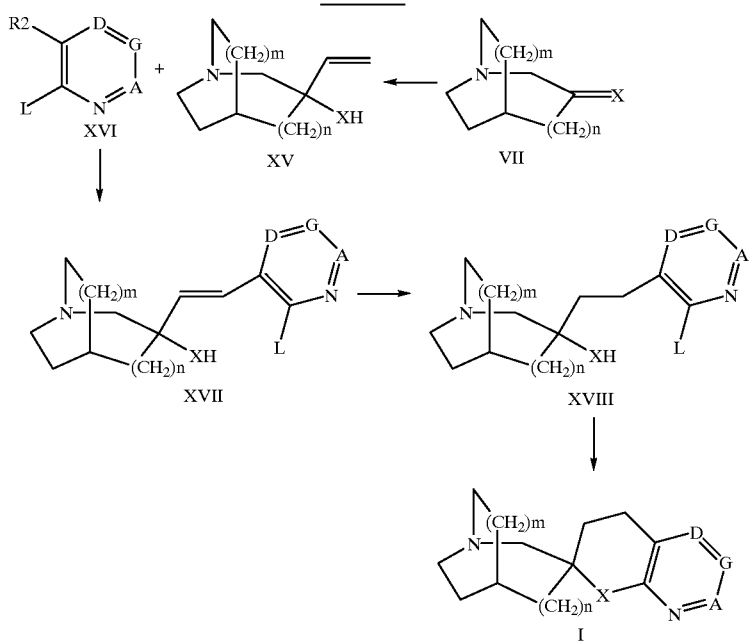

Compounds of formula I where W is $H_2$ and p is 1 may be prepared from the deprotection of a compound of formula IX using acid in a suitable solvent. Suitable acids include mineral, organic and Lewis acids, for example, hydrochloric and hydrobromic acid, sulfuric acid, triflic acid, methanesulfonic acid and borontrifluoride etherate. The preferred acid is hydrobromic acid. Suitable solvents include acetone, butanone, ethanone, and pinacolone. The preferred solvent is acetone. The reaction is usually conducted at a temperature from about −10° C. to about 100° C., preferably about 0° C. to about 60° C. Alternatively the deprotection may be conducted by heating the borane complex in alcoholic solvents. A preferred method is by refluxing a ethanolic solution of the complex.

Compounds of formula I where W=O and p is 1 may be prepared by the oxidation of compounds of formula I, where W is $H_2$ and p is 1, using selenium dioxide, or by reaction first with N-bromosuccinimide then with sodium bicarbonate and methylsulfoxide, followed by removal of the borane group as described above.

Compounds of formula I, where $W=F_2$ and p is 1, may be prepared from compounds of formula I, where $W=O$ and p is 1, by reaction with diethylaminosulfur trifluoride.

Compounds of formula IX may be prepared from the cyclization of a compound of formula X wherein L is fluoro, chloro, bromo, iodo, —$OCH_3$, —SPh, —$SCH_3$, —$SO_2Ph$, or —$SO_2CH_3$ in the presence of a base in an inert solvent. Suitable bases include sodium hydride, sodium amide, potassium hydride, potassium t-amylate, potassium t-butoxide, and potassium bis(trimethylsilyl)amide. The preferred base is sodium hydride. Suitable inert solvents include N,N-dimethylformamide, N-methylpyrrolidin-2-one, ethers such as diethyl ether, tetrahydrofuran, and 1,4-dioxane, and dimethylsulfoxide. The preferred inert solvent is N,N-dimethylformamide. The reaction is usually conducted at a temperature from about $-10°$ C. to about $100°$ C., preferably about $20°$ C. to about $66°$ C.

Compounds of formula X wherein L is fluoro, chloro, bromo, iodo, —$OCH_3$, —SPh, —$SCH_3$, —$SO_2CH_3$ may be prepared by the reaction of a compound of formula XI with a compound of formula V wherein L is defined as above in an inert solvent. Suitable inert solvents include diethyl ether, tetrahydrofuran and 1,4-dioxane. The preferred inert solvent is tetrahydrofuran. The reaction is usually conducted at a temperature from about $-100°$ C. to about $0°$ C., preferably about $-78°$ C. to about $-25°$ C.

Compounds XI, wherein P is —$SO_2Ph$, —$SO_2PhCH_3$-4, —$SO_2CH_3$ or —$SO_2CF_3$ may be prepared from compounds XII by reaction with a reagent such as toluenesulfonyl chloride, methanesulfonyl chloride, or trifluoromethanesulfonyl chloride in the presence of an amine base such as triethylamine, dimethylaminopyridine, or diazabicyclo[4.3.0]nonane in an inert solvent. Suitable inert solvents may be dichloromethane, chloroform, tetrahydrofuran, diethyl ether, or dioxane. The preferred inert solvent is dichloromethane. The reaction is usually conducted at a temperature from about $-10°$ C. to about $66°$ C., preferably about $0°$ C. to about $20°$ C.

Compounds XII may be prepared from compounds of formula XIII by reduction with reagents such as lithium aluminum hydride, sodium bis(2-methoxyethoxy)aluminum hydride, sodium or lithium triethylboride, lithium tri-sec-butylborohydride, potassium tri-sec-butylborohydride, sodium tri-sec-butylborohydride or lithium borohydride. The preferred reagent is lithium borohydride. Suitable inert solvents include diethyl ether, tetrahydrofuran and 1,4-dioxane. The preferred inert solvent is tetrahydrofuran. The reaction is usually conducted at a temperature from about $-78°$ C. to about $66°$ C., preferably about $-10°$ C. to about $20°$ C.

Compounds of formula XIII, wherein R is $C_1$–$C_6$ alkyl, —$CH_2$-Ar, or Ar, where Ar is phenyl optionally substituted with one to three of the following substitutents: halogen, $C_1$–$C_4$ alkyl, or $C_1$–$C_4$ alkoxy, may be prepared from the reaction of a compound of formula XIV with borane ($BH_3$ or $B_2H_6$) in an inert solvent. Borane in tetrahydrofuran is preferred. Suitable inert solvents include diethyl ether, tetrahydrofuran and 1,4-dioxane. The preferred inert solvent is tetrahydrofuran. The reaction is usually conducted at a temperature from about $-10°$ C. to about $66°$ C., preferably about $0°$ C. to about $20°$ C.

Compounds of formula XIV are known, e.g., either commercially available or may be prepared from compounds of formula VII by methods known to one skilled in the art for the preparation of β-hydroxy esters from the reaction of esters and ketones (see, e.g. the reactions referenced in J. March, "Advanced Organic Chemistry" (1985) 3rd Edition, page 439).

Compounds of formula I where W is $H_2$ and p is 1 may be prepared from the cyclization of a compound of formula XVIII wherein L is fluoro, chloro, bromo, iodo, —$OCH_3$, —SPh, —$SCH_3$, —$SO_2Ph$, or —$SO_2CH_3$ in the presence of a base in an inert solvent. Suitable bases include sodium hydride, sodium amide, potassium hydride, potassium t-amylate, potassium t-butoxide, and potassium bis (trimethylsilyl)amide. The preferred base is sodium hydride. Suitable inert solvents include N,N-dimethylformamide, N-methylpyrrolidin-2-one, ethers such as diethyl ether, tetrahydrofuran, and 1,4-dioxane, and dimethylsulfoxide. The preferred inert solvent is N,N-dimethylformamide. The reaction is usually conducted at a temperature from about $-10°$ C. to about $100°$ C., preferably about $20°$ C. to about $66°$ C.

Compounds of formula XVIII wherein L is defined as above may be prepared by catalytic hydrogenation of a compound of formula XVII using catalysts such as palladium on carbon, palladium hydroxide on carbon, palladium oxide, platinum on carbon, platinum oxide, Raney nickel, or rhenium on carbon in an inert solvent. Suitable inert solvents include methanol, ethanol, aqueous methanol or ethanol and ethyl acetate. The preferred solvent is ethanol. The reaction is usually conducted at a temperature from about $0°$ C. to about $100°$ C., preferably about $20°$ C. to about $50°$ C.

Compounds of formula XVII wherein L is defined as above may be prepared by reaction of a compound of formula XV with a compound of formula XVI using a palladium catalyst, together with a suitable ligand, base, and solvent. Suitable palladium catalysts include palladium acetate. Suitable ligands include phosphine ligands, such as triphenylphosphine or tri-o-tolylphosphine. Suitable bases include amines and inorganic bases, such as triethylamine, diisopropylethylamine, sodium carbonate or tetrabutylammonium acetate. Suitable solvents include dimethylformamide or acetonitrile. The reaction is usually conducted at a temperature from about $0°$ C. to about $140°$ C., preferably about $20°$ C. to about $85°$ C.

Compounds of formula XVI, where L is defined as above and $R^2$ is chloro, bromo, iodo, fluoro, trifluoromethylsulfonyl, toluenesulfonyl or methylsulfonyl may be prepared by literature methods from commercially available materials.

Compounds of formula XV may be prepared from compounds of formula VII by methods known to one skilled in the art for the preparation of allyl alcohols from ketones using vinylmetal salts such as vinylmagnesium bromide.

(C) Compounds wherein p is 0 or 1.

Compounds of formula I wherein $R^2$, $R^3$, or $R^4$ is halogen may be prepared from compounds of formula I wherein the corresponding substituent is hydrogen by reaction with a suitable halogenating agent, for example bromine in acetic acid. The transformation may require the addition of an acidic catalyst, such as the corresponding iron trihalide.

Compounds of formula I wherein $R^2$, $R^3$, or $R^4$ is $C_1$–$C_4$ alkyl, $C_2$–$C_4$ alkenyl, $C_2$–$C_4$ alkynyl, aryl, heteroaryl may be prepared from compounds of formula I wherein the corresponding substituent is halogen or $OSO_2CF_3$ by reaction with an appropriate alkyl, alkenyl, alkynyl, aryl or heteroaryl stannane reagent, in the presence of a suitable organometallic catalyst, for example tetrakis (triphenylphosphine)palladium (0), in a suitable solvent, for example 1,2-dimethoxyethane.

Compounds of formula I wherein $R^2$, $R^3$, or $R^4$ is aryl, heteroaryl may be prepared from compounds of formula I wherein the corresponding substituent is halogen or $OSO_2CF_3$ by reaction with an aryl or heteroaryl boronic acid, in the presence of a suitable organometallic catalyst, for example tetrakis(triphenylphosphine)palladium (0), in a suitable solvent, for example 1,2-dimethoxyethane.

Compounds of formula I wherein $R^2$, $R^3$, or $R^4$ is $NO_2$ may be prepared from compounds of formula I wherein the corresponding substituent is hydrogen by nitration using a suitable nitrating agent, for example nitric acid in concentrated sulfuric acid.

Compounds of formula I wherein $R^2$, $R^3$, or $R^4$ is $NH_2$ may be prepared from compounds of formula I wherein the corresponding substituent is $NO_2$ by reduction using a suitable procedure, for example hydrogenation. Hydrogenation may be performed by the reaction of a compound, dissolved in a suitable solvent, with gaseous hydrogen in the presence of a suitable catalyst. Suitable solvents include methanol, ethanol, and acetic acid. Suitable catalysts include palladium, for example as 10% palladium on carbon.

Compounds of formula I wherein $R^2$, $R^3$, or $R^4$ is $NR^5R^6$ wherein $R^6$ is alkyl may be prepared from compounds of formula I wherein the corresponding substituent is $NHR^5$ by a suitable alkylation procedure. Also, compounds of formula I wherein $R^2$, $R^3$, or $R^4$ is $NR^5R^6$ wherein $R^5$ and $R^6$ are identical alkyl groups or $R^5$ and $R^6$ together are $(CH_2)_jQ(CH_2)_k$ may be prepared from compounds of formula I wherein the corresponding substituent is $NH_2$ by a suitable alkylation procedure. Suitable alkylation procedures may include treatment with a suitable alkyl halide or sulfonate ester and base, for example sodium hydride, in a suitable solvent, for example DMF, or treatment with a suitable aldehyde or ketone in the presence of an acidic catalyst, for example zinc chloride, a reducing agent, for example sodium cyanoborohydride, and solvent, for example ethanol.

Compounds of formula I wherein $R^2$, $R^3$, or $R^4$ is $OSO_2CF_3$ may be prepared from compounds of formula I wherein the corresponding substituent is OH by reaction with trifluoromethanesulfonic anhydride in the presence of a suitable base, for example 2,6-di-t-butylpyridine, in a suitable solvent, for example dichloromethane.

Compounds of formula I wherein $R^2$, $R^3$, or $R^4$ is $NR^5R^6$ may also be prepared from compounds of formula I wherein the corresponding substituent is halide or $OSO_2CF_3$ by substitution with the appropriate amine $NHR^5R^6$. Suitable procedures include nucleophilic displacement, involving treatment with the amine, in excess or in the presence of an added base, and a suitable solvent, for example DMSO, or organometallic complex catalysed substitution, involving treatment with the amine in the presence of a suitable organometallic complex, for example complexes of palladium with chelating phosphine ligands, as described in J. Org. Chem., 1996, vol. 61, pp. 7240.

Compounds of formula I wherein $R^2$, $R^3$, or $R^4$ is $NR^5C(O)R^7$ may be prepared from compounds of formula I wherein the corresponding substituent is $NH_2$ by a suitable acylation procedure. Suitable acylation procedures include treatment with a carboxylic acid chloride $R^6C(O)Cl$ in the presence of an optional nucleophilic catalyst, such as 4-(N,N-dimethylamino)pyridine, a base, for example pyridine or triethylamine, and a suitable solvent, for example tetrahydrofuran, or, alternatively, treatment with a carboxylic acid $R_6C(O)OH$ with a coupling agent, for example 1,3-dicyclohexylcarbodiimide, in a suitable solvent, for example tetrahydrofuran.

Compounds of formula I wherein $R^2$, $R^3$, or $R^4$ is $NR^5C(O)NHR^8$ may be prepared from compounds of formula I wherein the corresponding substituent is $NHR^5$ by treatment with the appropriate isocyanate $R^8NCO$ in a suitable solvent, for example tetrahydrofuran.

Compounds of formula I wherein $R^2$, $R^3$, or $R^4$ is $NR^5C(O)OR^9$ may be prepared from compounds of formula I wherein the corresponding substituent is $NHR^5$ by treatment with an appropriate oxychloride or carbonate in the presence of an optional nucleophilic catalyst, such as 4-(N,N-dimethylamino)pyridine, a base, for example pyridine or triethylamine, and a suitable solvent, for example tetrahydrofuran.

Compounds of formula I wherein $R^2$, $R^3$, or $R^4$ is $NR^5SO_2R^{10}$ may be prepared from compounds of formula I wherein the corresponding substituent is $NHR^5$ by treatment with an appropriate sulfonyl chloride in a suitable solvent, such as pyridine.

Compounds of formula I wherein $R^2$, $R^3$, or $R^4$ is CN may be prepared from compounds of formula I wherein the corresponding substituent is halide or $OSO_2CF_3$ by reaction with a cyanide salt, in a suitable solvent, with the addition of a suitable catalyst possibly also being required. Suitable cyanide salts include copper (I) cyanide, sodium cyanide, sodium dicyanocuprate, or potassium cyanide, and suitable solvents include N,N-dimethylformamide, dimethylsulfoxide, or pyridine. Catalysts which may facilitate the transformation include copper (I) oxide, tetrakis (triphenylphosphine)palladium (0), or nickel (0) complexes generated in situ from dibromobis(triphenylphosphine) nickel(ii), zinc and triphenylphosphine.

Compounds of formula I wherein $R^2$, $R^3$ or $R^4$ is OH, $OC_1$–$C_4$ alkyl may be prepared either from an appropriately substituted 2-chloropyridine or via chemical transformation from another substituent e.g; the OH derivative from the $NH_2$ via the diazo intermediate.

Where necessary, hydroxy, amino, or other reactive groups may be protected using a protecting group as described in the standard text "Protecting Groups in Organic Synthesis", $2^{nd}$ Edition (1991) by Greene and Wuts.

Compounds of Formula I may be prepared from other compounds of Formula I by using general methods known to one skilled in the art for interconversion of functional groups (see, e.g. the reactions referenced in J. March, "Advanced Organic Chemistry" (1985) 3rd Edition).

Also, several of the substituted compounds of Formula I may be prepared by using an appropriately substituted compound of Formula VIII, viz., 2-chloro-5-trifluoromethylpyridine would yield the $R^3$ is $CF_3$.

The above described reactions, unless otherwise noted, are usually conducted at a pressure of about one to about three atmospheres, preferably at ambient pressure (about one atmosphere). Unless otherwise stated, the above described reactions are conducted under an inert atmosphere, preferably under a nitrogen atmosphere.

The compounds of the invention and intermediates may be isolated from their reaction mixtures by standard techniques.

Acid addition salts of the compounds of formula I which may be mentioned include salts of mineral acids, for example the hydrochloride and hydrobromide salts; and salts formed with organic acids such as formate, acetate, maleate, benzoate, tartrate, and fumarate salts.

Acid addition salts of compounds of formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

The compounds of formula I exist in tautomeric or enantiomeric forms, all of which are included within the scope of the invention. The various optical isomers may be isolated by separation of a racemic mixture of the compounds using conventional techniques, e.g. fractional crystallization, or chiral HPLC. Alternatively the individual enantiomers may be made by reaction of the appropriate optically active starting materials under reaction conditions which will not cause racemization.

(D) Compounds wherein Y is NO

Compounds of formula I, wherein Y is NO, X is oxygen, A is $C(R^2)$, G is $C(R^3)$ and D is $C(R^4)$, may be prepared from compounds of formula XIX, wherein X is oxygen, A is $C(R^2)$, G is $C(R^3)$ and D is $C(R^4)$, by reduction with a suitable reducing agent under suitable conditions, for example sulfur dioxide in ethanol at ambient temperature.

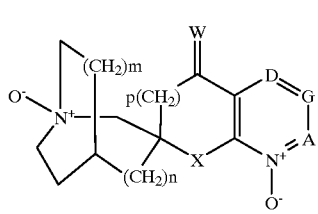

XIX

Compounds of formula XIX may be prepared from compounds of formula I wherein Y is N, X is oxygen, A is $C(R^2)$, G is $C(R^3)$ and D is $C(R^4)$, by oxidation with a suitable oxidising agent under suitable conditions, for example aqueous hydrogen peroxide in acetic acid at reflux temperature.

Compounds of the formula I wherein Y is N, X is oxygen, A is $C(R^2)$, G is $C(R^3)$ and D is $C(R^4)$, may be prepared in analogy with sections (A), (B) and (C), above.

Compounds of formula I, in which Y is N and A is $C(R^2)$, wherein $R^2$ is hydroxyl, may be prepared from compounds of formula I in which Y is NO by rearrangement using a carboxylic anhydride in a suitable solvent, for example trifluoroacetic anhydride in DMF;

Compounds of formula I in which Y is N and A is $C(R^2)$, wherein $R^2$ is halogen, may be prepared from compounds of formula I in which Y is NO and A is $C(R^2)$, wherein $R^2$ is hydrogen, by reaction with a phosphorus halide or oxyhalide, either neat or with a suitable co-solvent, for example neat phosphorus oxychloride.

Compounds of formula I in which Y is N and A is $C(R^2)$, wherein $R^2$ is CN, may be prepared from compounds of formula I in which Y is NO and A is $C(R^2)$, wherein $R^2$ is hydrogen, by reaction with a suitable cyanide source such as trimethylsilyl cyanide in the presence of a suitable base, for example triethylamine, in a suitable solvent, for example acetonitrile.

Intermediates

A further aspect of the invention relates to new intermediates. Special interest among these new intermediates are the borane containing compounds, especially the compound of formula II in Scheme I and the compound of formula XIII in Scheme II. These intermediates are useful in the synthesis of compounds of formula I, but their use is not limited to the synthesis of said compounds;

Thus, compounds of the formula II

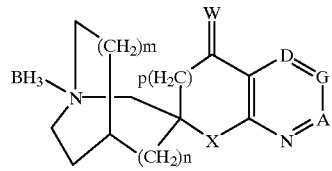

II wherein n is 0 or 1;
m is 0 or 1;
p is 0 or 1;
X is oxygen or sulfur;
W is oxygen, $H_2$ or $F_2$;
A is N or $C(R^2)$;
G is N or $C(R^3)$;
D is N or $C(R^4)$;
with the proviso that no more than one of A, G, and D is nitrogen;
$R^1$ is hydrogen or $C_1$–$C_4$ alkyl;
$R^2$, $R^3$, and $R^4$ are independently hydrogen, halogen, $C_1$–$C_4$ alkyl, $C_2$–$C_4$ alkenyl, $C_2$–$C_4$ alkynyl, aryl, heteroaryl, OH, $OC_1$–$C_4$ alkyl, $CO_2R^1$, —CN, —$NO_2$, —$NR^5R^6$, —$CF_3$, —$OSO_2CF_3$ or $R^2$ and $R^3$, or $R^3$ or $R^4$, respectively, may together form another six membered aromatic or heteroaromatic ring sharing A and G, or G and D, respectively, containing between zero and two nitrogen atoms, and substituted with one to two of the following substituents: independently hydrogen, halogen, $C_1$–$C_4$ alkyl, $C_2$–$C_4$ alkenyl, $C_2$–$C_4$ alkynyl, aryl, heteroaryl, OH, $OC_1$–$C_4$ alkyl, $CO_2R_1$, —CN, —$NO_2$, —$NR^5R^6$, —$CF_3$, —$OSO_2CF_3$;
$R^5$ and $R^6$ are independently hydrogen, $C_1$–$C_4$ alkyl, $C(O)R^7$, $C(O)NHR^8$, $C(O)OR^9$, $SO_2R^{10}$ or may together be $(CH_2)_jQ(CH_2)_k$ where Q is O, S, $NR^{11}$, or a bond;
j is 2 to 7;
k is 0 to 2;
$R^7$, $R^8$, $R^9$, $R^{10}$, and $R^{11}$ are independently $C_1$–$C_4$ alkyl, aryl, or heteroaryl, or an enantiomer thereof.

Compounds of formula XIII

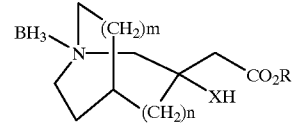

XIII wherein n is 0 or 1;
m is 0 or 1;
X is oxygen or sulfur;
$R^1$ is hydrogen or $C_1$ to $C_4$ alkyl;
R is $C_1$–$C_6$ alkyl, —$CH_2$-Ar, or Ar;
Ar is phenyl optionally substituted with one to three of the following substitutents: halogen, $C_1$–$C_4$ alkyl, or $C_1$–$C_4$ alkoxy, or an enantiomer thereof.

Intermediate compounds also exist in enantiomeric forms and may be used as purified enantiomers, racemates or mixtures.

Use of compounds IV, III, II, XIII, X and IX as intermediates in a synthesis of a ligand for nicotinic acetylcholine receptors is another aspect of the invention.

A further aspect of the invention relates to the utility of compounds of formula I wherein Y is NO as intermediates. These intermediates are useful in the synthesis of compounds of formula I wherein Y is N, but their use is not limited to the synthesis of said compounds.

Pharmaceutical Compositions

A further aspect of the invention relates to a pharmaceutical composition for treating or preventing a condition or disorder as exemplified below arising from dysfunction of nicotinic acetylcholine receptor neurotransmission in a mammal, preferably a human, comprising an amount of a compound of formula I, an enantiomer thereof or a pharmaceutically acceptable salt thereof, effective in treating or preventing such disorder or condition and an inert pharmaceutically acceptable carrier.

For the above-mentioned uses the dosage administered will, of course, vary with the compound employed, the mode of administration and the treatment desired. However, in general, satisfactory results are obtained when the compounds of the invention are administered at a daily dosage of from about 0.1 mg to about 20 mg per kg of animal body weight, preferably given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carrier or diluent.

The compounds of formula I, or an enantiomer thereof, and pharmaceutically acceptable salts thereof, may be used on their own or in the form of appropriate medicinal preparations for enteral or parenteral administration. According to a further aspect of the invention, there is provided a pharmaceutical composition including preferably less than 80% and more preferably less than 50% by weight of a compound of the invention in admixture with an inert pharmaceutically acceptable diluent or carrier.

Examples of diluents and carriers are:
for tablets and dragees: lactose, starch, talc, stearic acid;
for capsules: tartaric acid or lactose;
for injectable solutions: water, alcohols, glycerin, vegetable oils; for suppositories: natural or hardened oils or waxes.

There is also provided a process for the preparation of such a pharmaceutical composition which comprises mixing the ingredients.

Utility

A further aspect of the invention is the use of a compound according to the invention, an enantiomer thereof or a pharmaceutically acceptable salt thereof, in the manufacture of a medicament for the treatment or prophylaxis of one of the below mentioned diseases or conditions; and a method of treatment or prophylaxis of one of the above mentioned diseases or conditions, which comprises administering a therapeutically effective amount of a compound according to the invention, or an enantiomer thereof or a pharmaceutically acceptable salt thereof, to a patient.

Compounds according to the invention are agonists of nicotinic acetylcholine receptors. While not being limited by theory, it is believed that agonists of the α7 nAChR (nicotinic acetylcholine receptor) subtype should be useful in the treatment or prophylaxis of psychotic disorders and intellectual impairment disorders, and have advantages over compounds which are or are also agonists of the α4 nAChR subtype. Therefore, compounds which are selective for the α7 nAChR subtype are preferred. The compounds of the invention are indicated as pharmaceuticals, in particular in the treatment or prophylaxis of psychotic disorders and intellectual impairment disorders. Examples of psychotic disorders include schizophrenia, mania and manic depression, and anxiety. Examples of intellectual impairment disorders include Alzheimer's disease, learning deficit, cognition deficit, attention deficit, memory loss, and Attention Deficit Hyperactivity Disorder. The compounds of the invention may also be useful as analgesics in the treatment of pain (including chronic pain) and in the treatment or prophylaxis of Parkinson's disease, Huntington's disease, Tourette's syndrome, and neurodegenerative disorders in which there is loss of cholinergic synapses. The compounds may further be indicated for the treatment or prophylaxis of jetlag, for use in inducing the cessation of smoking, and for the treatment or prophylaxis of nicotine addiction (including that resulting from exposure to products containing nicotine).

It is also believed that compounds according to the invention are useful in the treatment and prophylaxis of ulcerative colitis.

Pharmacology

The pharmacological activity of the compounds of the invention may be measured in the tests set out below:

Test A—Assay for affinity at α7 nAChR subtype $_{125}$I-α-Bungarotoxin (BTX) binding to rat hippocampal membranes. Rat hippocampi were homogenized in 20 volumes of cold homogenization buffer (HB: concentrations of constituents (mM): tris(hydroxymethyl)aminomethane 50; $MgCl_2$ 1; NaCl 120; KCl 5: pH 7.4). The homogenate was centrifuged for 5 minutes at 1000 g, the supernatant was saved and the pellet re-extracted. The pooled supernatants were centrifuged for 20 minutes at 12000 g, washed, and resuspended in HB. Membranes (30–80 μg) were incubated with 5 nM [$^{125}$I]α-BTX, 1 mg/mL BSA (bovine serum albumin), test drug, and either 2 mM $CaCl_2$ or 0.5 mM EGTA [ethylene glycol-bis(β-aminoethylether)] for 2 hours at 21° C., and then filtered and washed 4 times over Whatman glass fibre filters (thickness C) using a Brandel cell harvester. Pretreating the filters for 3 hours with 1% (BSA/0.01% PEI (polyethyleneimine) in water was critical for low filter blanks (0.07% of total counts per minute). Nonspecific binding was described by 100 μM (−)-nicotine, and specific binding was typically 75%.

Test B—Assay for affinity to the α4 nAChR subtype

[$^3$H]-(−)-nicotine binding. Using a procedure modified from Martino-Barrows and Kellar (Mol Pharm (1987) 31:169–174), rat brain (cortex and hippocampus) was homogenized as in the [$_{125}$I]α-BTX binding assay, centrifuged for 20 minutes at 12,000×g, washed twice, and then resuspended in HB containing 100 μM diisopropyl fluorophosphate. After 20 minutes at 4° C., membranes (approximately 0.5 mg) were incubated with 3 nM [3H]-(−)-nicotine, test drug, 1 μM atropine, and either 2 mM $CaCl_2$ or 0.5 mM EGTA for 1 hour at 4° C., and then filtered over Whatman glass fibre filters (thickness C) (pretreated for 1 hour with 0.5% PEI) using a Brandel cell harvester. Nonspecific binding was described by 100 μM carbachol, and specific binding was typically 84%.

Binding Data Analysis for Tests A and B $IC_{50}$ values and pseudo Hill coefficients ($n_H$) were calculated using the non-linear curve fitting program ALLFIT (DeLean A, Munson P J and Rodbard D (1977) Am. J. Physiol., 235:E97-E102). Saturation curves were fitted to a one site model, using the non-linear regression program ENZFITTER (Leatherbarrow, R. J. (1987)), yielding $K_D$ values of 1.67 and 1.70 nM for the $^{125}$I-α-BTX and [$^3$H]-(−)-nicotine ligands respectively. $K_i$ values were estimated using the general Cheng-Prusoff equation:

$K_i=[IC_{50}]/((2+([ligand]/[K_D])_n)^{1/n}-1)$ where a value of n=1 was used whenever $n_H<1.5$ and a value of n=2 was used when $n_H \geq 1.5$. Samples were assayed in triplicate and were typically ±5%. $K_i$ values were determined using 6 or more drug concentrations. The compounds of the invention are compounds with binding affinities ($K_i$) of less than 1000 nM in either Test A or Test B, indicating that they are expected to have useful therapeutic activity.

The compounds of the invention have the advantage that they may be less toxic, be more efficacious, be longer acting, have a broader range of activity, be more potent, produce fewer side effects, are more easily absorbed or have other useful pharmacological properties.

EXAMPLES

Commercial reagents were used without further purification. Mass spectra were recorded using either a Hewlett Packard 5988A or a MicroMass Quattro-1 Mass Spectrometer and are reported as m/z for the parent molecular ion with its relative intensity. Room temperature refers to 20–25° C.

Preparation 1

Spiro[1-azabicyclo[2.2.2]octane-3,2'-oxirane]N-borane complex

A mixture of trimethylsulfoxonium iodide (16.10 g, 73.2, mmol) and a dispersion of sodium hydride (60% in oil, 3.00 g, 75.0 mmol) in anhydrous dimethyl sulfoxide was stirred at room temperature under nitrogen for 30 minutes. Quinuclidin-3-one (7.05 g, 56.3 mmol) was then added as a solid portionwise, and the resulting mixture was stirred at 65–70° C. under nitrogen for 1 hour. The reaction mixture was cooled, water was added (200 mL), and the resulting solution was extracted with chloroform (3×200 mL). The chloroform extracts were combined, and back-extracted with water (4×200 mL). The chloroform layer was then dried (MgSO$_4$), filtered, and evaporated under reduced pressure to afford spiro[1-azabicyclo[2.2.2]octane-3,2'-oxirane] (6.51 g, 46.8 mmol, 83%) as a clear, colorless liquid. To a stirred solution of spiro[1-azabicyclo[2.2.2]octane-3,2'-oxirane] (5.3 g, 38.1 mmol) in anhydrous tetrahydrofuran (100 mL) at 0° C. was added dropwise a solution of borane in tetrahydrofuran (1.0 M, 38.1 mL, 38.1 mmol), and resulting solution was stirred at 0° C. under nitrogen for 30 minutes. Brine (100 mL) was added cautiously to the reaction solution, and the resulting aqueous mixture was extracted with ethyl acetate (2×100 mL). The organic extracts were combined, dried (MgSO$_4$), filtered, and evaporated under reduced pressure to afford the title compound (4.3 g, 28.1 mmol, 74%) as a white solid: electrospray MS 152 ([M-H]$^+$, 15).

Preparation 2

3-(2-Chloropyridin-3-ylmethyl)-3-hydroxy-1-azabicyclo[2.2.2]octane N-borane complex A solution of phenyllithium (1.8 M in cyclohexane/ether [7:3], 167 mL, 0.3 mol, 3 eq.) was added via a cannula to anhydrous tetrahydrofuran (350 mL) at −40° C. under a nitrogen atmosphere. Then, diisopropylamine (0.7 mL, 5 mmol) was added dropwise, followed by a dropwise addition of 2-chloropyridine (28.4 mL, 0.3 mol, 3 eq.) over ten minutes. The resulting solution was stirred at −40° C. under nitrogen for 1.5 hours. The solution was then cooled to −60° C., and a solution of spiro[1-azabicyclo[2.2.2]octane-3,2'-oxirane]N-borane complex (15.3 g, 0.1 mol) in tetrahydrofuran (75 mL) was added dropwise. The resulting reaction mixture was then stirred at −40° C. under nitrogen. After 3 hours, a saturated solution of sodium bicarbonate (150 mL) was slowly added, followed by water (400 mL), and the resulting aqueous mixture was allowed to warm to room temperature. The layers were separated and the aqueous phase was extracted with ethyl acetate (3×100 mL). The organic layers were combined, dried (MgSO$_4$), filtered, and evaporated under reduced pressure. Column chromatography using silica gel and elution with ethyl acetate/hexanes [3:2] afforded the title compound as a tan solid (17.5 g, 65.6 mmol, 66%): electrospray MS 269 ([MH]$^+$ with $^{37}$Cl, 10), 267 ([MH]$^+$ with $^{35}$Cl, 26).

Preparation 2(b)

3-(2,4-Dichloropyridin-3-ylmethyl)-3-hydroxy-1-azabicyclo[2.2.2]octane N-borane complex was prepared from 2.64 g (17.8 mmol) of 2,4-dichloropyridine and 1.37 g (8.95 mmol) of spiro[1-azabicyclo[2.2.2]octane-3, 2'oxirane], providing 2.42 g (90%), m.p. 178–179° C. (1:1 ethyl acetate-hexane)

Preparation 3

Spiro[1-azabicyclo[2.2.2]octane-3,2'(3'H)-furo[2,3-b]pyridine]N-borane complex 3-(2-Chloropyridin-3-ylmethyl)-3-hydroxy-1-azabicyclo [2.2.2]octane N-borane complex (17.4 g, 65.3 mmol) was dissolved in anhydrous N,N-dimethylformamide (500 mL), the resulting solution was cooled to 0° C. under nitrogen, and a dispersion of sodium hydride (60% in oil, 6.55 g, 163 mmol, 2.5 eq.) was added portionwise. The resulting solution was stirred at room temperature under nitrogen for 16 hours. A saturated solution of ammonium chloride (50 mL) was then added at 0° C., followed by ice water (500 mL), and the resulting aqueous mixture was extracted with chloroform (4×125 mL). The organic extracts were combined, dried (MgSO$_4$), and evaporated under reduced pressure to afford an orange solid. Purification through a short column of silica gel eluting with chloroform/acetone [95:5 to 85:15], followed by stirring in hexanes (100 mL) and filtration, provided a yellow solid (12.7 g, 55.2 mmol, 84%) of the title compound: electrospray MS 231 ([MH]$^+$, 65).

Preparation 4

3-(2-Methanesulfonyloxyethyl)-3-trimethylsilyloxy-1-azabicyclo[2.2.2]octane N-borane complex (a) 2-(3-Hydroxy-1-azabicyclo[2.2.2]oct-3-yl)acetic acid t-butyl ester To a solution of diisopropylamine (6.7 mL) in tetrahydrofuran (THF) (20 mL) at 0° C. was added n-butyllithium (2.3M in hexanes; 20 mL). The reaction mixture was stirred for 40 minutes and then cooled to −78° C. To this mixture a solution of t-butyl acetate (6.4 mL) in THF (10 mL) was added dropwise and stirring was continued for an additional 15 minutes. Quinuclidin-3-one (5 g) in THF (15 mL) was added to the mixture dropwise and the mixture was allowed to warm to 0° C. over 1 hour. To this solution water (100 mL) was added, the solution was extracted twice with chloroform and the combined extracts were washed once with brine. The resulting solution was dried over MgSO$_4$, filtered, and evaporated in vacuo to give 9.53 g of the subtitle compound as an off-white solid.

(b) 2-(3-Hydroxy-1-azabicyclo[2.2.2]oct-3-yl)acetic acid methyl ester

Trifluoroacetic acid (40 mL) was added dropwise over 15 minutes to a solution of 2-(3-hydroxy-1-azabicyclo[2.2.2]

oct-3-yl)acetic acid t-butyl ester (15.7 g) in anhydrous dichloromethane (40 mL) at 0° C. The mixture was stirred for 24 hours at room temperature, then the solvent was evaporated under reduced pressure. The residue was dissolved in methanol (90 mL) and cooled in an ice bath. Concentrated sulfuric acid (9 mL) was added dropwise over 10 minutes, then the reaction mixture was stirred at room temperature. After 3 hours, the solution was poured into 100 mL of ice water, basified to pH 10 with saturated aqueous sodium carbonate solution, and extracted with chloroform (4×100 mL). The extracts were dried (MgSO$_4$), filtered, and evaporated in vacuo to give a solid. Recrystallization from ethyl acetate provided 6.3 g of the tan crystalline subtitle compound.

(c) 2-(3-Hydroxy-1-azabicyclo[2.2.2]oct-3-yl)acetic acid methyl ester N-borane complex Borane in THF (1M, 5.25 mL) was added dropwise over 20 minutes to a solution of 2-(3-hydroxy-1-azabicyclo [2.2.2]oct-3-yl)acetic acid methyl ester (1 g) in anhydrous tetrahydrofuran (THF) (20 mL) stirred at 0° C. After 30 minutes, 20 mL of brine was added, stirring was continued for a further 30 minutes and the layers were then separated. The aqueous layer was extracted with ethyl acetate (2×20 mL), the organic layers were combined, and then dried (MgSO$_4$), filtered, and evaporated under reduced pressure. The residue was subjected to flash chromatography on silica gel (eluting with chloroform/acetone, 95:5) to give the title compound (900 mg) as an off-white solid.

(d) 3-Hydroxy-3-(2-hydroxyethyl)-1-azabicyclo [2.2.2]octane N-borane complex

Under an argon atmosphere, lithium borohydride (2M in tetrahydrofuran, 2.6 mL, 5.2 mmol) was added over 5 minutes to a solution of 2-(3-hydroxy-1-azabicyclo[2.2.2] oct-3-yl)acetic acid methyl ester N-borane complex (1 g, 4.7 mmol) in anhydrous tetrahydrofuran (20 mL) and heated at reflux for 1 hour. The reaction was cooled (ice bath), quenched with water (5 mL) and saturated aqueous sodium bicarbonate (5 mL), stirred for 45 minutes at 0° C. to room temperature, and extracted four times with ethyl acetate. The combined organic layers were dried (MgSO$_4$), evaporated under reduced pressure and triturated with ethyl ether to obtain the title compound (830 mg, 4.5 mmol, 95%) as a white solid.

(e) 3-Trimethylsilyloxy-3-(2-trimethylsilyloxyethyl)-1-azabicyclo[2.2.2]octane N-borane complex Under an argon atmosphere, chlorotrimethylsilane (0.255 mL, 2 mmol) was added via syringe over 5 minutes to 3-hydroxy-3-(2-hydroxyethyl)-1-azabicyclo[2.2.2]octane N-borane complex (185 mg, 1 mmol) in dry 1-methylimidazole (1 mL) at 0° C. N-(trimethylsilyl) acetamide (262 mg, 2 mmol) was added in one portion, the reaction was stirred for 16 hours at room temperature and heated at 55–60° C. for 3 hours. The mixture was cooled, poured into ice/water (5 g), and extracted four times with ether. The combined organic layers were washed four times with brine, dried (MgSO$_4$), evaporated under reduced pressure and purified by flash chromatography (eluting with hexane/ethyl acetate, 3:2) to obtain the title compound (210 mg, 0.64 mmol, 64%).

(f) 3-(2-Hydroxyethyl)-3-trimethylsilyloxy-1-azabicyclo[2.2.2]octane N-borane complex Under an argon atmosphere, 3-trimethylsilyloxy-3-(2-trimethylsilyloxyethyl)-1-azabicyclo[2.2.2]octane N-borane complex (190 mg, 0.58 mmol) in anhydrous methanol (1 mL) containing 0.032 M potassium carbonate in methanol (0.25 mL) was stirred at room temperature for 84 hours, acidified to pH 7 with acetic acid, and evaporated under reduced pressure. Purification by flash chromatography (eluting with hexane/ethyl acetate, 3:2) provided the title compound (94 mg, 0.37 mmol, 63%).

(g) 3-(2-Methanesulfonyloxyethyl)-3-trimethylsilyloxy-1-azabicyclo[2.2.2]octane N-borane complex Under an argon atmosphere, methanesulfonyl chloride (0.086 mL, 1.1 mmol) in anhydrous pyridine (1 mL) was added over 20 minutes at 0° C.–5° C. to a solution of 3-(2-hydroxy-ethyl)-3-trimethylsilyloxy-1-azabicyclo [2.2.2]octane N-borane complex (257 mg, 1 mmol) in anhydrous pyridine (4 mL), stirred at 0° C. for 20 minutes, and at room temperature for 2 hours. Poured into ice (15 g), extracted four times with ethyl acetate, combined the organic layers, and washed sequentially with 1 N aqueous hydrochloric acid (three times), water, and saturated aqueous sodium bicarbonate. The extracts were dried (MgSO$_4$), evaporated under reduced pressure and purified by flash chromatography (eluting with chloroform/ethyl acetate, 97:3) to obtain the title compound (263 mg, 0.78 mmol, 78%).

Preparation 5

(a) 3-Ethenyl-3-hydroxy-1-azabicyclo[2.2.2]octane

Under an argon atmosphere, a solution of 3-quinuclidinone (1.25 g, 10 mmol) in anhydrous tetrahydrofuran (10 mL) was added over 15 minutes to a 1 M solution of vinylmagnesium bromide in tetrahydrofuran (20 mL, 20 mmol) at 0° C. to 5° C., stirred at room temperature for 24 hours, cooled to 0° C., and acidified to pH 1 with 6 M hydrochloric acid. The mixture was stirred for 15 minutes, basified to pH 10 with 25% aqueous sodium hydroxide, extracted with chloroform (4×50 mL) and chloroform/methanol (4:1, 50 mL), combined the organic layers, dried (MgSO$_4$), evaporated under reduced pressure and purified by flash chromatography (eluting with ammoniated chloroform/methanol, 85:15) to obtain the title compound (830 mg, 5.4 mmol, 54%).

(b) 3-Bromo-2-hydroxypyridine

A solution of bromine (9.6 g, 60 mmol) in 1 M aqueous potassium bromide (120 mL) was added over 5 minutes to a solution of 2-hydroxypyridine (5.7 g, 60 mmol) in 1 M aqueous potassium bromide (60 mL) and stirred for 24 hours. The solid precipitate was filtered off, the aqueous phase was saturated with sodium chloride and extracted with chloroform (4×20 mL), the combined extracts were dried (MgSO$_4$), evaporated under reduced pressure and combined with the original precipitate. Purification by flash chromatography (eluting with ammoniated chloroform/methanol, 95:5) and recrystallization from acetonitrile provided the title compound (3.62 g, 20.8 mmol, 35%).

(c) 3-Bromo-2-methoxypyridine

Under an argon atmosphere, a mixture of 3-bromo-2-hydroxypyridine (3.49 g, 20 mmol), silver carbonate (3.67 g, 13.31 mmol), and iodomethane (1.5 mL, 24.1 mmol) in benzene (30 mL) was stirred in the dark at 40° C. to 50° C. for 24 hours, cooled in an ice bath, and filtered. The filtrate was washed once with 2% aqueous sodium bicarbonate and twice with water, dried (MgSO$_4$), the benzene was evaporated at atmospheric pressure, and the residue was purified by flash chromatography (eluting with hexane/ethyl acetate, 2:1) to obtain the title compound (2.35 g, 12.5 mmol, 62%).

Example 1

Spiro[1-azabicyclo[2.2.2]octane-3,2'(3'H)-furo[2,3-b]pyridine]

5'-Spiro[1-azabicyclo[2.2.2]octane-3,2'(3'H)-furo[2,3-b]pyridine]N-borane complex (12.2 g, 53 mmol) was dissolved in 150 mL of acetone, the solution was cooled to 0° C., and an aqueous solution of HBr (24%; 50 mL) was added. The resulting solution was stirred at room temperature under nitrogen for 24 hours. The reaction was concentrated under reduced pressure, and the aqueous residue was treated with saturated aqueous sodium carbonate solution (50 mL). The solution was basified to pH>10 using solid sodium carbonate, and the resulting solution was extracted with chloroform (3×100 mL). The organic extracts were combined, dried (MgSO$_4$), filtered, and evaporated under reduced pressure to afford the title compound (11.2 g, 51.8 mmol, 98%, 54% overall) as an off-white solid: electrospray MS 217 ([MH]$^+$, 72).

The title compound was separated into its (R)- and (S)-enantiomers by either of the following methods:

Method A—250 mg of the title compound was separated by chiral HPLC, using a 2 cm×25 cm CHIRALCEL-OD column on a Waters Delta Prep 3000 Preparative Chromatography System, eluting with 2,2,4-trimethylpentane/ethanol (92:8 to 9:1) at a flow rate of 20 mL/min. This provided 111 mg of the (S)-enantiomer ([α]$^{23}$=+59.7° (c=1, methanol)) and 90 mg of the (R)-enantiomer ([α]$^{23}$=−63.9° (c=1, methanol)).

Method B—1 g (4.62 mmol) of the title compound was treated with L-(+)-tartaric acid (694 mg; 4.62 mmol) in 15% aqueous ethanol (10 mL) and recrystallized three times to obtain the (S)-enantiomer L-(+)-tartrate (650 mg; 1.77 mmol; [α]$^{23}$=+57.7° (c=2, H$_2$O)). The filtrates were concentrated under reduced pressure and the aqueous residue was basified to pH>10 using solid sodium carbonate. The resulting mixture was extracted with chloroform (3×25 mL) and the combined extracts were dried (MgSO$_4$), and evaporated under reduced pressure. The residue (650 mg; 3 mmol) was treated with D-(−)-tartaric acid (452 mg; 3 mmol) and recrystallized as above to provide the (R)-enantiomer D-(−)-tartrate (775 mg; 2.11 mmol; [α]$^{23}$=−58.2° (c=2, H$_2$O)).

Example 2A

5'-Bromospiro[1-azabicyclo[2.2.2]octane-3,2'(3'H)-furo[2,3-b]pyridine]

A solution of spiro[1-azabicyclo[2.2.2]octane-3,2'(3'H)-furo[2,3-b]pyridine] (100 mg, 0.462 mmol) and sodium acetate (410 mg, 5 mmol) in 50% aqueous acetic acid (4 mL) was heated to 60° C. Bromine (0.100 mL, 1.94 mmol) was added via a syringe over 10 minutes, and the solution was then heated under reflux for 1 hour. The mixture was allowed to cool to ambient temperature, basified to pH>10 with sodium carbonate, and extracted with chloroform (3×15 mL). The combined extracts were dried (MgSO$_4$), filtered, and evaporated under reduced pressure to give the title compound (110 mg, 0.37 mmol, 81%) as an off-white solid: electrospray MS 295 ([MH]$^+$, with $^{79}$Br, 100), 297 ([MH]$^+$, with $^{81}$Br, 98).

Example 2B (R)-(−)-5'-Bromospiro[1-azabicyclo[2.2.2]octane-3,2'(3'H)-furo[2,3-b]pyridine]

The enantiomer (R)-(−)-spiro[1-azabicyclo[2.2.2]octane-3,2'(3'H)-furo[2,3-b]pyridine] (1.95 g, 9 mmol) treated in the same way as described in example 2A provided the title compound (1.77 g, 6 mmol, 67%) ([α]$^{23}$=−45.5° (c=1, MeOH)).

Example 3

5'-Phenylspiro[1-azabicyclo[2.2.2]octane-3,2'(3'H)-furo[2,3-b]pyridine]

Under a nitrogen atmosphere, 5'-bromospiro[1-azabicyclo [2.2.2]octane-3,2'(3'H)-furo[2,3-b]pyridine] (118 mg, 0.4 mmol), phenylboronic acid (54 mg, 0.443 mmol), and tetrakis(triphenylphosphine)palladium(0) (11 mg, 2.3 mol %) were stirred in a solution of 1,2-dimethoxyethane (3 mL) and ethanol (0.75 mL) containing 2M aqueous sodium carbonate (0.65 mL, 1.3 mmol). The mixture was heated under reflux for 18 hours. The reaction mixture was then evaporated under reduced pressure, the residue was dissolved in chloroform (15 mL), and the extract was washed with saturated aqueous sodium carbonate (5 mL). The aqueous layer was extracted with chloroform (2×15 mL), and the organic layers were combined, dried (MgSO$_4$), filtered, and evaporated under reduced pressure. Purification by flash chromatography through silica gel, eluting with ammoniated chloroform/methanol (95:5 to 9:1), provided the title compound (80 mg, 0.274 mmol, 68%) as a tan solid: electrospray MS 293 ([MH]$^+$, 100).

Example 4A

5'-Nitrospiro[1-azabicyclo[2.2.2]octane-3,2'(3'H)-furo[2,3-b]pyridine]

A mixture of spiro[1-azabicyclo[2.2.2]octane-3,2'(3'H)-furo[2,3-b]pyridine] (325 mg, 1.5 mmol) and fuming nitric acid (0.27 mL, 5.74 mmol) in sulfuric acid (0.75 mL) was heated at 70° C. to 80° C. for 24 hours. The resulting viscous solution was poured onto 15 g of ice and basified to pH>10 with solid sodium carbonate. The resulting mixture was extracted with chloroform (4×15 mL), dried (MgSO$_4$), filtered, and evaporated under reduced pressure. Purification by flash chromatography through silica gel, eluting with ammoniated chloroform/methanol (95:5), provided the title compound (200 mg, 0.765 mmol, 51%) as a light yellow solid: electrospray MS 262 ([MH]$^+$, 100).

Example 4B (R)-(−)-5'-Nitrospiro[1-azabicyclo[2.2.2]octane-3,2' (3'H)-furo[2,3-b]pyridine]

(R)-(−)-Spiro[1-azabicyclo[2.2.2]octane-3,2'(3'H)-furo [2,3-b]pyridine] (3.03 g, 14 mmol) was dissolved in concentrated sulfuric acid (7 mL) at 0–5° C., fuming nitric acid (3.3 mL, 70.2 mmol) was added over 10 minutes, the mixture was stirred for 1 hour, and heated at 65–70° C. for 24 hours. Cooled, poured onto ice (200 gm), added 300 mL of water, basified to pH 10 with solid potassium carbonate, stirred for 1 hour, filtered off and dried the solid title compound (3.6 g, 13.8 mmol, 98%): electrospray MS (m/z, relative intensity) 262 ([MH]$^+$, 100).

Example 4C (S)-(+)-5'-Nitrospiro[1-azabicyclo[2.2.2]octane-3,2' (3'H)-furo[2,3-b]pyridine]

The enantiomer (S)-(+)-spiro[1-azabicyclo[2.2.2]octane-3,2'(3'H)-furo[2,3-b]pyridine] (6.5 g, 30 mmol) treated in the same way as described in example 4B provided the title

Example 5

Spiro[1-Azabicyclo[2.2.2]octane-3,2'(3'H)-furo[2,3-b]quinoline]

The title compound was prepared by a procedure analogous to that described in Example 1 from 2-chloroquinoline (0.99 g, 6.06 mmol) and spiro[1-azabicyclo[2.2.2]octane-3,2'-oxirane]N-borane complex (0.31 g, 2.0 mmol), yielding the title compound (0.135 g) as a beige powder, electrospray MS 267 [MH]$^+$.

The two enantiomers were resolved on a Chiral OD column by elution with an 8–10% EtOH/hexane gradient, and UV detection. First enantiomer: 100% chiral purity by LC, Rt=12.32 minutes, $[\alpha]_D$ at 23° in EtOH=+47.9°. Second enantiomer: 99.4% chiral purity, Rt=17.84 minutes, $[\alpha]_D$=−48.5°.

Example 6

1'-Chlorospiro[1-azabicyclo[2.2.2]octane-3,2'(3'H)-furo[2,3-b]isoquinoline]

The title compound was prepared by a procedure analogous to that described in Example 1 from 1,3-dichloroisoquinoline (2.41 g, 12.2 mmol) and spiro[1-azabicyclo[2.2.2]octane-3,2'-oxirane]N-borane complex (0.62 g, 4.05 mmol), yielding 0.86 g of 1'-chlorospiro[1-azabicyclo[2.2.2]octane-3,2'(3'H)-furo[2,3-b]isoquinoline] N-borane complex, electrospray MS 314 [MH$^+$]. Removal of the borane group from 65 mg of the N-borane complex gave 30 mg of the title compound, electrospray MS 301 [MH$^+$].

Example 7

Spiro[1-azabicyclo[2.2.2]octane-3,2'(3'H)-furo[2,3-b]isoquinoline]

The borane protected chloride of Example 6 (0.3 g or 0.96 mmol) was suspended in a mixture of glacial acetic acid (6.0 ml) and water (0.5 ml). The suspension was placed under nitrogen and zinc dust (150 mg) was added. The reaction mixture was stirred at 70° C. for 5 hours. The reaction mixture was allowed to cool and was then poured into saturated NaHCO$_3$. Enough aqueous NaHCO$_3$ was added to give a basic pH, and the products were extracted with three portions of chloroform. The combined chloroform extract was dried (MgSO$_4$), filtered, and evaporated in vacuo. Two runs were combined for purification on a silica flash column, using a gradient from 2:1 hexane/ethyl acetate to 100% ethyl acetate. The faster eluting compound was spiro[1-azabicyclo[2.2.2]octane-3,2'(3'H)-furo[2,3-b]isoquinoline]N-borane complex and the slower eluting compound was the title compound. Yield 100%: chemical ionization MS 279 [MH]$^+$—H$_2$ for the N-borane complex and 267 [MH]$^+$ for the title compound. Removal of the borane group under the conditions of Example 1 followed by flash chromatography gave the title compound as a brown semi-solid: chemical ionization MS 267 [MH]$^+$.

Example 8A

5'-Aminospiro[1-azabicyclo[2.2.2]octane-3,2'(3'H)-furo[2,3-b]pyridine]

A mixture of 5'-nitrospiro[1-azabicyclo[2.2.2]octane-3,2'(3'H)-furo[2,3-b]pyridine] (1.4 g, 5.36 mmol), and 10% palladium on carbon (48% water wet, 270 mg) in methanol (90 mL) was hydrogenated for 1 hour at 50 psi of hydrogen. The catalyst was filtered off through a pad of celite and the solvent was evaporated under reduced to obtain the amine (1.2 g, 5.25 mmol, 98%) as a tan solid: electrospray MS (m/z, relative intensity) 232 ([MH]$^+$, 100).

The title compound was separated into its (R)- and (S)-enantiomers by the following method:

150 mg of the title compound was separated by chiral HPLC, using a 2 cm×25 cm CHIRALCEL-OD column on a Waters Delta Prep 4000 Preparative Chromatography System [hexane/ethanol (85:15 to 8:2)] at a flow rate of 20 mL/min. This provided 52 mg of the (S)-epimer ($[\alpha]^{22}$=+62° (c=1, ethanol) and 52 mg of the (R)-epimer ($[\alpha]^{23}$=−64° (c=1, ethanol).

Example 8B (R)-(−)-5'-Aminospiro[1-azabicyclo-[2.2.2]octane-3,2'(3'H)-furo[2,3-b]pyridine]

The enantiomer (R)-(−)-5'-nitrospiro[1-azabicyclo[2.2.2]octane-3,2'(3'H)-furo[2,3-b]pyridine] (3.8 g, 13.3 mmol) treated in the same way as described in example 8A, and purified by flash chromatography (eluting with ammoniated chloroform/methanol, 95:5 to 85:15), provided the title compound (2.5 g, 10.8 mmol, 81%): electrospray MS (m/z, relative intensity) 232 ([MH]$^+$, 100).

Example 8C (S)-(+)-5'-Aminospiro[1-azabicyclo-[2.2.2]octane-3,2'(3'H)-furo[2,3-b]pyridine]

The enantiomer (S)-(+)-5'nitrospiro[1-azabicyclo[2.2.2]octane-3,2'(3'H)-furo[2,3-b]pyridine] (6.85 g, 26.2 mmol) treated in the same way as described in example 8A in ammoniated methanol provided the title compound (5.55 g, 24 mmol, 92%): electrospray MS (m/z, relative intensity) 232 ([MH]$^+$, 100).

Example 9

5'-Phenylcarboxamidospiro[1-azabicyclo[2.2.2]octane-3,2'(3'H)-furo[2,3-b]pyridine]

Under a nitrogen atmosphere, benzoic acid (67 mg, 0.55 mmol), O-(1H-benzotriazol-1-yl)-N,N,N'N'-tetramethyluronium tetrafluoroborate ("TBTU", 176 mg, 0.55 mmol), 1-hydroxybenzotriazole hydrate ("HOBT", 78 mg, 0.55 mmol), and diisopropylethylamine (0.193 mL, 1.1 mmol) were combined in anhydrous N,N-dimethylformamide (8 mL) and stirred for 10 minutes. 5'-Aminospiro[1-azabicyclo[2.2.2]octane-3,2'(3'H)-furo[2,3-b]pyridine] (115 mg, 0.5 mmol) was added as a solid in one portion and stirring was continued for 3 days. The solvent was evaporated under high vacuum to 55° C. and the residue was partitioned between saturated aqueous sodium carbonate (2 mL) and dichloromethane (10 mL). After separating, the aqueous layer was extracted with dichloromethane (2×5 mL). The organic layers were combined, dried (MgSO$_4$), and evaporated under reduced pressure. Purification by flash chromatography through silica gel, eluting with ammoniated chloroform/methanol (9:1), provided the title compound (125 mg, 0.372 mmol, 75%) as a yellow solid: electrospray MS (m/z, relative intensity) 336 ([MH]$^+$, 100).

Example 10

5'-Phenylaminocarbonylaminospiro[1-azabicyclo[2.2.2]octane-3,2'(3'H)-furo[2,3-b]pyridine]

Under a nitrogen atmosphere, phenyl isocyanate (0.056 mL, 0.515 mmol) was added to a suspension of 5'-aminospiro[1-azabicyclo[2.2.2]octane-3,2'(3'H)-furo[2,3-b]pyridine] (119 mg, 0.514 mmol) in anhydrous tetrahydrofuran (5 mL) and stirred for 12 hours. The solvent was evaporated under reduced pressure and the residue purified by flash chromatography through silica gel, eluting with ammoniated chloroform/methanol (92.5:7.5), to obtain the title compound (155 mg, 0.442 mmol, 86%) as an off-white solid: electrospray MS (m/z, relative intensity) 351 ([MH]$^+$, 100).

Example 11

5'-Phenylsulfonylamidospiro[1-azabicyclo[2.2.2]octane-3,2'(3'H)-furo[2,3-b]pyridine]

Under a nitrogen atmosphere, benzenesulfonyl chloride (0.07 mL, 0.55 mmol) was added to a solution of 5'-aminospiro[1-azabicyclo[2.2.2]octane-3,2'(3'H)-furo[2,3-b]pyridine] (115 mg, 0.5 mmol) in anhydrous pyridine (5 mL) and stirred for 4 hours. The solvent was evaporated under high vacuum, the residue was partitioned between saturated aqueous sodium carbonate (2 mL) and chloroform (10 mL), separated and extracted the aqueous phase with chloroform (2×5 mL). The combined organic layers were dried (MgSO$_4$), the solvent was evaporated under reduced pressure, and the residue was re-evaporated from ethanol (3×10 mL) under reduced pressure. This afforded the title compound (179 mg, 0.5 mmol, 100%) as a yellow solid: electrospray MS (m/z, relative intensity) 372 ([MH]$^+$, 100).

Example 12

5'-(N-Methylamino)spiro[1-azabicyclo[2.2.2]octane-3,2'(3'H)-furo[2,3-b]pyridine]

Under a nitrogen atmosphere, sodium (50 mg, 2.17 mmol) was slowly added (exothermic) to methanol (1 mL) and stirred for 1 hour. 5'-Aminospiro[1-azabicyclo[2.2.2]octane-3,2'(3'H)-furo[2,3-b]pyridine] (115 mg, 0.5 mmol) and paraformaldehyde (35 mg, 1.17 mmol) were added and stirred for 16 hours. The reaction was heated at 50° C. for 4 hours, sodium borohydride (53 mg, 1.4 mmol) was added, and heated at reflux for 1 hour. Then, 1 N aqueous potassium hydroxide (0.4 mL) was added and continued at reflux for 2 hours more. The solvent was evaporated under reduced pressure, the residue was partitioned between water (1 mL) and chloroform (4 mL), separated and extracted the aqueous phase with chloroform (2×4 mL). The combined organic layers were washed with brine (1 mL), dried (MgSO$_4$), evaporated under reduced pressure, and purified by flash chromatography through silica gel (eluting with ammoniated chloroform/methanol, 95:5) to obtain the title compound (78 mg, 0.32 mmol, 64%) as an off-white solid: electrospray MS (m/z, relative intensity) 246 ([MH]$^+$, 100).

Example 13A

5'-(N,N-Dimethylamino)spiro[1-azabicyclo[2.2.2]octane-3,2'(3'H)-furo[2,3-b]pyridine]

Sodium cyanoborohydride (63 mg, 1 mmol) was dissolved in methanol (2.5 mL), anhydrous zinc chloride (69 mg, 0.5 mmol) was added, stirred for 30 minutes, added the resulting solution to a solution of 5'-aminospiro[1-azabicyclo[2.2.2]octane-3,2'(3'H)-furo[2,3-b]pyridine] (115 mg, 0.5 mmol) and 37% aqueous formaldehyde (0.12 mL, 1.6 mmol) in methanol (2.5 mL), and stirred for 20 hours. Poured into 1 N aqueous potassium hydroxide (10 mL), stirred for 1 hour, evaporated under reduced pressure, and extracted the aqueous residue with chloroform (4×10 mL). The combined extracts were dried (MgSO$_4$), evaporated under reduced pressure, and purified by flash chromatography through silica gel (eluting with ammoniated chloroform/methanol, 97.5:2.5), to obtain the title compound (85 mg, 0.33 mmol, 66%) as an off-white solid: electrospray MS (m/z, relative intensity) 260 ([MH]$^+$, 100).

Example 13B (R)-(−)-5'-(N,N-Dimethylamino)spiro[1-azabicyclo[2.2.2]octane-3,2'(3'H)-furo[2,3-b]pyridine]

The enantiomer (R)-(−)-5'-aminospiro[1-azabicyclo[2.2.2]octane-3,2'(3'H)-furo[2,3-b]pyridine] (231 mg, 1 mmol) treated in the same way as described in example 13A provided the title compound (178 mg, 0.69 mmol, 69%): electrospray MS (m/z, relative intensity) 260 ([MH]$^+$, 100).

Example 14A (S)-(+)-5'-(E)-(Phenylethenyl)spiro[1-azabicyclo[2.2.2]octane-3,2'(3'H)-furo[2,3-b]pyridine]

A solution of (S)-(+)-5'-bromospiro[1-azabicyclo[2.2.2]octane-3,2'(3'H)-furo[2,3-b]pyridine] (150 mg, 0.51 mmol), styrene (0.07 mL, 0.61 mmol), palladium(II)acetate (1.2 mg, 0.0053 mmol), tri-o-tolylphosphine (6.4 mg, 0.021 mmol), and triethylamine (0.5 mL, 3.6 mmol) in anhydrous acetonitrile (0.5 mL), in a heavy-walled threaded glass tube containing a magnetic stir bar, was purged with argon and sealed with a Teflon plug and FETFE O-ring. The mixture was stirred and heated at 100° C. for 2 hours, cooled to room temperature, dissolved in chloroform (10 mL), washed with saturated aqueous sodium carbonate (1 mL), dried (MgSO$_4$), and evaporated under reduced pressure. Recrystallization from ethyl acetate afforded the title compound (90 mg, 0.28 mmol, 55%) as a light tan solid: electrospray MS (m/z, relative intensity) 319 ([MH]$^+$, 100).

Example 14B (R)-(−)-5'-(E)-(Phenylethenyl)spiro[1-azabicyclo[2.2.2]octane-3,2'(3'H)-furo[2,3-b]pyridine]

Treatment of the enantiomer (R)-(−)-5'-bromospiro[1-azabicyclo[2.2.2]octane-3,2'(3'H)-furo[2,3-b]pyridine] (295 mg, 1 mmol) in the same way as described in example 14A, and purification by flash chromatography (eluting with ammoniated chloroform/methanol, 98:2 to 96:4) provided the title compound (132 mg, 0.41 mmol, 41%): electrospray MS (m/z, relative intensity) 319 ([MH]$^+$, 100).

Example 15A (S)-(+)-5'-(4-Morpholino)spiro[1-azabicyclo[2.2.2]octane-3,2'(3'H)-furo[2,3-b]pyridine]

Sodium tert-butoxide (56.6 mg, 0.59 mmol), tris(dibenzylideneacetone)dipalladium (15.4 mg, 0.017 mmol), and 2,2'-bis(diphenylphosphino)-1,1'-binaphthyl (21 mg, 0.034 mmol) were combined in a heavy-walled threaded glass tube containing a magnetic stir bar, and purged with argon. Added (S)-(+)-5'-bromospiro[1-azabicyclo[2.2.2]octane-3,2'(3'H)-furo[2,3-b]pyridine] (130 mg, 0.44 mmol), morpholine (0.066 mL, 0.76 mmol) and anhydrous tetrahydrofuran (3 mL), sealed with a Teflon plug and FETFE O-ring, stirred and heated at 100° C. for 72 hours. The mixture was cooled to room temperature, dissolved in chloroform (25 mL), washed with brine (3×2 mL), dried (MgSO$_4$), evaporated under reduced pressure, purified by flash chromatography through silica gel (eluting with ammoniated ether/methanol, 4:1), and recrystallized from ethyl acetate to obtain the title compound (35 mg, 0.12 mmol, 26%) as a tan solid: electrospray MS (m/z, relative intensity) 302 ([MH]$^+$, 100).

Example 15B (R)-(-)-5'-(4-Morpholino)spiro[1-azabicyclo[2.2.2] octane-3,2'(3'H)-furo[2,3-b]pyridine]

Treatment of the enantiomer (R)-(-)-5'-bromospiro[1-azabicyclo[2.2.2]octane-3,2'(3'H)-furo[2,3-b]pyridine] (580 mg, 1.965 mmol) in the same way as described in example 15A, provided the title compound (187 mg, 0.62 mmol, 32%): electrospray MS (m/z, relative intensity) 302 ([MH]$^+$, 100).

Example 16

(R)-(-)-5'-(1-Azetidinyl)spiro[1-azabicyclo[2.2.2] octane-3,2'(3'H)-furo[2,3-b]pyridine]

(R)-(-)-5'-Bromospiro[1-azabicyclo[2.2.2]octane-3,2' (3'H)-furo[2,3-b]pyridine] (295 mg, 1 mmol), azetidine (0.101 mL, 1.5 mmol), sodium tert-butoxide (135 mg, 1.4 mmol), tris(dibenzylideneacetone)dipalladium (46 mg, 0.05 mmol), 2,2'-bis(diphenylphosphino)-1,1'-binaphthyl (62 mg, 0.1 mmol) and anhydrous tetrahydrofuran (9 mL) were combined in a heavy-walled threaded glass tube containing a magnetic stir bar, purged with argon, and sealed with a Teflon plug and FETFE O-ring. The mixture was stirred and heated at 75° C. for 4 hours, cooled to room temperature, dissolved in chloroform (20 mL), washed with brine (3×10 mL), dried (MgSO$_4$), evaporated under reduced pressure, and purified by flash chromatography through silica gel (eluting with ammoniated chloroform/methanol 95:5) to procure the title compound (230 mg, 0.0.85 mmol, 85%) as a light tan solid: chemical ionization MS (m/z, relative intensity) 272 ([MH]$^+$, 56).

Example 17

(R)-(-)-5'-(2-(4-Pyridyl)ethenyl)spiro[1-azabicyclo [2.2.2]octane-3,2'(3'H)-furo[2,3-b]pyridine]

(R)-(-)-5'-Bromospiro[1-azabicyclo[2.2.2]octane-3,2' (3'H)-furo[2,3-b]pyridine] (295 mg, 1 mmol),4-vinylpyridine (0.135 mL, 1.25 mmol), palladium(II)acetate (7.2 mg,0.032 mmol), tri-o-tolylphosphine (38.7 mg, 0.127 mmol), and triethylamine (0.5 mL, 3.6 mmol) in anhydrous acetonitrile (0.5 mL) were combined in a heavy-walled threaded glass tube containing a magnetic stir bar, purged with argon and sealed with a Teflon plug and FETFE O-ring. The mixture was stirred and heated at 100 to 105° C. for 48 hours, cooled to room temperature, dissolved in chloroform (25 mL), washed with saturated aqueous sodium carbonate (2 mL), dried (MgSO$_4$), and evaporated under reduced pressure. Purification by flash chromatography through silica gel (eluting with ammoniated chloroform/methanol, 95:5), followed by recrystallization from acetone afforded the title compound (230 mg, 0.72 mmol, 72%): electrospray MS (m/z, relative intensity) 320 ([MH]$^+$, 100).

Example 18

(R)-(-)-5'-(2-(2-Pyridyl)ethenyl)spiro[1-azabicyclo [2.2.2]octane-3,2'(3'H)-furo[2,3-b]pyridine]

(R)-(-)-5'-Bromospiro[1-azabicyclo[2.2.2]octane-3,2' (3'H)-furo[2,3-b]pyridine] (150 mg, 0.5 mmol) was treated with 2-vinylpyridine (0.070 mL, 0.65 mmol) in the same way as described in example 16. Purification by flash chromatography through silica gel (eluting with ammoniated ether/methanol, 95:5 to 9:1), followed by recrystallization from acetonitrile produced the title compound (37 mg, 0.12 mmol, 23%): electrospray MS (m/z, relative intensity) 320 ([MH]$^+$, 100).

Example 19

(R)-(-)-5'-(2-Trimethylsilylethynyl)spiro[1-azabicyclo[2.2.2]octane-3,2'(3'H)-furo[2,3-b] pyridine]

(R)-(-)-5'-Bromospiro[1-azabicyclo[2.2.2]octane-3,2' (3'H)-furo[2,3-b]pyridine](295 mg, 1 mmol), trimethylsilylacetylene (0.355 mL, 2.5 mmol), tetrakis (triphenylphosphine)palladium (230 mg, 0.2 mmol), triethylamine (2 mL) and anhydrous acetonitrile (2 mL) were combined in a heavy-walled threaded glass tube containing a magnetic stir bar, purged with argon and sealed with a Teflon plug and FETFE O-ring. The mixture was stirred and heated at 100° C. for 4 hours, cooled to room temperature, dissolved in chloroform (25 mL), washed with saturated aqueous sodium carbonate (2 mL), dried (MgSO$_4$), and evaporated under reduced pressure. Purification by flash chromatography through silica gel (eluting with ammoniated ether/methanol, 9:1) afforded the title compound (280 mg, 0.90 mmol, 90%): chemical ionization MS (m/z, relative intensity) 313 ([MH]$^+$, 30).

Example 20

(R)-(-)-5'-Ethynylspiro[1-azabicyclo[2.2.2]octane-3, 2'(3'H)-furo[2,3-b]pyridine]

Under an argon atmosphere, a 1 M solution of tetrabutylammonium fluoride in tetrahydrofuran (1.3 mL, 1.3 mmol) was added at 0° C. to a solution of (R)-(-)-5'-(2-trimethylsilylethynyl)spiro[1-azabicyclo[2.2.2]octane-3,2' (3'H)-furo[2,3-b]pyridine] (265 mg, 0.85 mmol) in anhydrous tetrahydrofuran (5 mL), and stirred at room temperature for 2 hours. The reaction was quenched with saturated aqueous ammonium chloride solution (2 mL), extracted with ether (5×15 mL), dried (MgSO$_4$), evaporated under reduced pressure, and purified by flash chromatography through silica gel (eluting with ammoniated chloroform/methanol, 95:5) to obtain the title compound (121 mg, 0.50 mmol, 59%): chemical ionization MS (m/z, relative intensity) 241 ([MH]$^+$, 19).

Example 21

5'-(2-Furyl)spiro[1-azabicyclo[2.2.2]octane-3,2' (3'H)-furo[2,3-b]pyridine]

A solution containing 5'-bromospiro[1-azabicyclo[2.2.2] octane-3,2'(3'H)-furo[2,3-b]pyridine] (103.5 mg, 0.351 mmol), tris(dibenzylidineacetone)dipalladium (0) (14 mg, 0.015 mmol), tri(o-tolyl)phosphine (44.4 mg, 0.146 mmol), lithium chloride (62 mg, 1.46 mmol), and 2-(tri-n-butylstannyl)furan (0.17 g, 0.476 mmol) in 1,2-dimethoxyethane (1 ml) was heated under reflux for 2 h. The solution was evaporated, and the residue was taken up in chloroform and filtered. The filtrate was evaporated then purified by HPLC using a gradient of 0–25% 1:1:2 7M methanolic ammonia:methanol:chloroform and chloroform to obtain the title compound (89 mg, 0.313 mmol, 89%) as a pale solid: electrospray MS (m/z, relative intensity) 283 ([MH]$^+$, 100).

Example 22

5'-(3-Pyridyl)spiro[1-azabicyclo[2.2.2]octane-3,2'(3'H)-furo[2,3-b]pyridine]

A solution containing 5'-bromospiro[1-azabicyclo[2.2.2]octane-3,2'(3'H)-furo[2,3-b]pyridine] (158 mg, 0.535 mmol), tris(dibenzylidineacetone)dipalladium (0) (23 mg, 0.025 mmol), tri(o-tolyl)phosphine (66 mg, 0.217 mmol), lithium chloride (99 mg, 2.34 mmol), and 3-(tri-n-butylstannyl)pyridine (0.3 ml, approx. 0.3 g, approx. 0.82 mmol) in 1,2-dimethoxyethane (2 ml) was heated under reflux for 6 h. The solution was evaporated, and the residue was taken up in chloroform and filtered. The filtrate was evaporated then purified by HPLC using a gradient of 0–20% 1:1:2 7M methanolic ammonia:methanol:chloroform and chloroform to obtain the title compound (58 mg, 0.198 mmol, 37%) as a pale solid: electrospray MS (m/z, relative intensity) 294 ([MH]$^+$, 80), 273 (100).

Example 23

5'-Methylspiro[1-azabicyclo[2.2.2]octane-3,2'(3'H)-furo[2,3-b]pyridine]

A solution containing 5'-bromospiro[1-azabicyclo[2.2.2]octane-3,2'(3'H)-furo[2,3-b]pyridine] (203 mg, 0.687 mmol), tris(dibenzylidineacetone)dipalladium (0) (33 mg, 0.036 mmol), tri(o-tolyl)phosphine (95 mg, 0.312 mmol), lithium chloride (241 mg, 5.69 mmol), and tetramethylstannane (0.1 ml, 1.3 g, 7.2 mmol) in 2-methoxyethyl ether (5 ml) was heated in a bath maintained at 100° C. After 3 h, a further portion of tetramethylstannane (1 ml, 1.3 g, 7.2 mmol) was added, and heating was continued overnight. The solution was filtered, and subjected to purification by HPLC using a gradient of 0–20% 1:1:2 7M methanolic ammonia:methanol:chloroform and chloroform to obtain the title compound (120 mg, 0.519 mmol, 76%) as a pale solid: electrospray MS (m/z, relative intensity) 231 ([MH]$^+$, 100).

Example 24

Spiro[1-azabicyclo[2.2.2]octane-3,2'(3'H)-furo[2,3-b]pyridine-5'-carbonitrile] and Spiro[1-azabicyclo[2.2.2]octane-3,2'(3'H)-furo[2,3-b]pyridine-5'-carboxamide]

A solution containing 5'-bromospiro[1-azabicyclo[2.2.2]octane-3,2'(3'H)-furo[2,3-b]pyridine] (165 mg, 0.558 mmol), and copper (I) cyanide (600 mg, 1.3 g, approx. 7.2 mmol) in 1-methyl-2-pyrrolidinone (5 ml) was heated in a bath maintained at 180° C. overnight and was then allowed to cool. The solution was then partitioned between aqueous ammonia and chloroform, and the organic layer was separated, then dried (magnesium sulfate), filtered, and evaporated. The residue was subjected to purification by HPLC using a gradient of 0–20% 1:1:2 7M methanolic ammonia:methanol:chloroform and chloroform to give spiro[1-azabicyclo[2.2.2]octane-3,2'(3'H)-furo[2,3-b]pyridine-5'-carbonitrile] (52 mg, 0.216 mmol, 39%) as a pale solid: DCI MS (m/z, relative intensity) 242 ([MH]$^+$, 100), and spiro[1-azabicyclo[2.2.2]octane-3,2'(3'H)-furo[2,3-b]pyridine-5'-carboxamide] (71 mg, 0.274 mmol, 49%) as a pale solid: electrospray MS (m/z, relative intensity) 260 ([MH]$^+$, 100).

Example 25

5'-Ethenylspiro[1-azabicyclo[2.2.2]octane-3,2'(3'H)-furo[2,3-b]pyrdine]

A solution containing 5'-bromospiro[1-azabicyclo[2.2.2]octane-3,2'(3'H)-furo[2,3-b]pyridine] (150 mg, 0.508 mmol), tris(dibenzylidineacetone)dipalladium (0) (22 mg, 0.024 mmol), tri(o-tolyl)phosphine (63 mg, 0.206 mmol), lithium chloride (103 mg, 2.43 mmol), and tri-n-butylvinylstannane (188 mg, 0.592 mmol) in 1,2-dimethoxyethane (10 ml) was heated under reflux overnight. The solution was evaporated, and the residue was taken up in chloroform and filtered. The filtrate was evaporated then purified by HPLC using a gradient of 0–25% 1:1:2 7M methanolic ammonia:methanol:chloroform and chloroform to obtain the title compound (93 mg, 0.385 mmol, 76%) as a pale solid: electrospray MS (m/z, relative intensity) 243 ([MH]$^+$, 100).

Example 26

(R)-(–)-5'-N'-(3-Chlorophenyl)aminocarbonylaminospiro[1-azabicyclo[2.2.2]octane-3,2'(3'H)-furo[2,3-b]pyridine]

The (R)-(–)-5'-Aminospiro[1-azabicyclo[2.2.2]octane-3,2'(3'H)-furo[2,3-b]pyridine] (65 mg or 0.28 mmoles) was suspended in 2.7 ml of anhydrous tetrahydrofuran under nitrogen atmosphere. The 3-chlorophenylisocyanate (35 μl) was added and the suspension was stirred at ambient temperature for 5 hours. The tetrahydrofuran was removed in vacuo and the crude was purified by flash chromatography. Elution with 20–40% methanol/chloroform (ammoniated with NH$_4$OH) gave the desired product spot product. The solvents were removed in vacuo and the residue was taken up in chloroform and dried (MgSO$_4$). Evaporating, chasing with two portions of ether, left 100 mg (92%) of white solid. Electrospray MS 385 and 387 [MH]$^+$.

Example 27

(R)-(–)-5'-N'-(2-Nitrophenyl)aminocarbonylaminospiro[1-azabicyclo[2.2.2]octane-3,2'(3'H)-furo[2,3-b]pyridine]

Using the same method as in example 27 but substituting 2-nitrophenyl isocyanate for 3-chlorophenylisocyanate the title compound was prepared; yield 97 mg (88%) of yellow powder. Electrospray MS 396 [MH]$^+$.

Example 28

(R)-(–)-5'-N,N-Diethylaminospiro[1-azabicyclo[2.2.2]octane-3,2'(3'H)-furo[2,3-b]pyridine]

Sodium cyanoborohydride (190 mg or 3.0 mmoles) and the zinc chloride (206 mg or 1.5 mmoles) were added to 3.0 mls of anhydrous methanol under nitrogen atmosphere. Stirring for 5 minutes gave complete dissolution. The (R)-(–)-5'-aminospiro[1-azabicyclo[2.2.2]octane-3,2'(3'H)-furo[2,3-b]pyridine] (230 mg or 1.0 mmol) was added followed by acetaldehyde (0.335 mls or 6.0 mmoles.) The suspension was stirred at ambient temperature for 16 hours. The methanol was concentrated in vacuo and the suspension was poured into 20 mls of 1 N sodium hydroxide. The aqueous layer was extracted with four 20 ml portions of chloroform, and these were combined dried (MgSO$_4$) and evaporated in vacuo. The crude was purified by flash chromatography, starting with 6/3/1/0.1 ethyl acetate/methanol/water (ammoniated with NH$_4$OH) and then to 3/6/1/0.1. The solvents were removed in vacuo and the residue was taken up in chloroform and dried (MgSO$_4$.) Obtained 0.227 g (79%) of light brown syrup. Electrospray MS 288 [MH]$^+$.

Example 29

(R)-(–)-5'-N-Ethylaminospiro[1-azabicyclo[2.2.2]octane-3,2'(3'H)-furo[2,3-b]pyridine]

(R)-(–)-5'-Aminospiro[1-azabicyclo[2.2.2]octane-3,2'(3'H)-furo[2,3-b]pyridine] (230 mg or 1.0 mmoles) and sodium cyanoborohydride were suspended in 6.2 mls of anhydrous methanol. The acetaldehyde (90 μl or 1.1 mmoles) and the solution was stirred at ambient temperature for 16 hours. The methanol was removed in vacuo and the residue was taken up in 2 mls of water and 8 mls of chloroform. The layers were separated and the aqueous layer was extracted 3 times more. The combined organic layers were dried (MgSO$_4$) and evaporated in vacuo. The crude product was purified by flash chromatography using a 3–15% methanol/chloroform (ammoniated) gradient. The solvents were evaporated in vacuo and chased with two portions of ether. The residue was suspended in ether and collected by filtration. After washing with ether and drying with high vacuum obtained 81 mg (31%) of white powder. Electrospray MS 260 [MH]$^+$.

Example 30

(R)-(−)-5'-N-Benzylaminospiro[1-azabicyclo[2.2.2] octane-3,2'(3'H)-furo[2,3-b]pyridine]

Prepared by the method of example 12. From 1.0 mmoles obtained 247 mg (77%) of white powder. Electrospray MS 322 [MH]$^+$.

Example 31

(R)-(−)-5'-N-Formamidospiro[1-azabicyclo[2.2.2] octane-3,2'(3'H)-furo[2,3-b]pyridine]

98% Formic acid (2.1 mls) and acetic anhydride (0.7 mls) were combined under nitrogen atmosphere and cooled with an ice bath. The (R)-(−)-5'-aminospiro[1-azabicyclo[2.2.2] octane-3,2'(3'H)-furo[2,3-b]pyridine] (230 mg or 1.0 mmoles) was added and the reaction was allowed to warm to ambient temperature. The reaction was stirred for 26 hours and then was poured with stirring into saturated sodium carbonate. Solid Na$_2$CO$_3$ was added until the pH was basic again, and then the aqueous layer was extracted with four portions of chloroform. These were combined, dried (MgSO$_4$,) and evaporated in vacuo. The crude was purified by flash chromatography eluting with a 2–10% ammoniated methanol/chloroform gradient. The solvents were removed in vacuo and the residue was taken up in chloroform, dried (MgSO$_4$) and evaporated in vacuo. The solvent was chased with two portions of ether giving 0.2 g (77%) of white solid. Electrospray MS 260 [MH]$^+$.

Example 32

(R)-(−)-5'-N-Acetamidospiro[1-azabicyclo[2.2.2] octane-3,2'(3'H)-furo[2,3-b]pyridine]

(R)-(−)-5'-Aminospiro[1-azabicyclo[2.2.2]octane-3,2' (3'H)-furo[2,3-b]pyridine] (230 mg or 1.0 mmoles) was dissolved in 3 mls anhydrous pyridine under nitrogen atmosphere. The acetic anhydride (0.1 mls or 1.1 mmoles) was added and the solution was heated at 100° C. for 40 hours. The pyridine was removed in vacuo, and the residue was taken up in 8 mls chloroform and washed with 4 mls of saturated sodium bicarbonate. The aqueous layer was extracted twice more with chloroform and the combined organic layers were dried (MgSO$_4$) and evaporated in vacuo. Purification by flash chromatography using a 3–20% ammoniated methanol/chloroform gradient gave the desired product. The solvents were removed in vacuo and chased with two portions of ether. Obtained 154 mg (56%) of white solid. Chemical ionization MS 274 [MH]$^+$.

Example 33

4'-Chlorospiro[1-azabicyclo[2.2.2]octane-3,2'(3'H)-furo[2,3-b]pyrdine] and 4'-chlorospiro[1-azabicyclo [2.2.2]octane-3,2'(3'H)-furo[3,2-c]pyridine]

4'-Chlorospiro[1-azabicyclo[2.2.2]octane-3,2'(3'H)-furo [2,3-b]pyridine]borane complex and 2'-chlorospiro[1-azabicyclo[2.2.2]octane-3,2'(3'H)-furo[3,2-c]pyridine] borane complex were prepared from 2.36 g (7.84 mmol) 3-(2,4-Dichloropyridin-3-ylmethyl)-3-hydroxy-1-azabicyclo[2.2.2]octane N-borane complex and 319 mg (7.97 mmol) of sodium hydride in dimethylformamide as in Preparation 2. This mixture was treated with aqueous hydrobromic acid in acetone to provide, following flash chromatography on neutral silica gel using a mixture of 98:2 ammoniated chloroform/methanol, 559 mg of 4'-chlorospiro [1-azabicyclo[2.2.2]octane-3,2'(3'H)-furo[2,3-b]pyridine], m.p. 109–110° C. (ethyl ether), and 463 mg of 4'-chlorospiro [1-azabicyclo[2.2.2]octane-3,2'(3'H)-furo[3,2-c]pyridine], m.p. 113–115° C.

Example 34

Spiro[1-azabicyclo[2.2.2]octane-3,2'(3'H)-furo[3,2-c]pyridine]

The 4'-chlorospiro[1-azabicyclo[2.2.2]octane-3,2'(3'H)-furo[3,2-c]pyridine] (125 mg or 5.0 mmol) from Example 33 was dissolved in 50 mL of anhydrous methanol, and 25 mg of 10% palladium on carbon was added. The bottle was placed on the Parr apparatus under hydrogen atmosphere and shaken for 2.5 hours. The Pd/C was removed by filtration and washed with methanol. The solvent was removed in vacuo and the residue was taken up in chloroform and methanol and transferred to a vial. The solvent was removed in vacuo and chased with two portions of ether. After drying with high vacuum obtained 112 mg of off-white powder (104% with residual solvent.) Electrospray MS 217 [MH]$^+$

Example 35

4'-Methoxyspiro[1-azabicyclo[2.2.2]octane-3,2' (3'H)-furo[2,3-b]pyridine]

Sodium hydride (241 mg, 6.0 mmol) was added to a solution of 76 mg (0.30 mmol) of 4'-chlorospiro[1-azabicyclo[2.2.2]octane-3,2'(3'H)-furo[2,3-b]pyridine] in 25 mL of ice-cold methanol, under a nitrogen atmosphere. The resulting solution was heated to reflux and stirred for 4 days, then cooled to ambient temperature, poured into 30 mL of water, and extracted with chloroform (3×30 mL). The combined organic extract was dried over anhydrous magnesium sulfate, concentrated in vacuo and the residue flash chromatographed on neutral silica gel using a 9:1 mixture of ammoniated chloroform/methanol to give 50 mg (67%) of the title compound as a white solid: electrospray MS (m/z, relative intensity) 247 ([MH]$^+$).

Example 36

4'-Phenylthiospiro[1-azabicyclo[2.2.2]octane-3,2' (3'H)-furo[2,3-b]pyridine]

Sodium hydride (151 mg, 3.77 mmol) was added to a solution of 97 mg (0.387 mmol) of 4'-chlorospiro[1-azabicyclo[2.2.2]octane-3,2'(3'H)-furo[2,3-b]pyridine], 0.40 mL (3.91 mmol) of thiophenol and 0.10 mL of methanol in 15 mL of dioxane, under a nitrogen atmosphere. The reaction was refluxed for 4 days, cooled to ambient temperature, diluted with 30 mL of water, and extracted with chloroform (3×30 mL). The combined organic extract was dried over anhydrous magnesium sulfate, concentrated in vacuo and the residue flash chromatographed on neutral silica gel using a 98:2 mixture of ammoniated chloroform/methanol to give 65 mg (52%) of the title compound as a colourless oil: electrospray MS (m/z, relative intensity) 325 ([MH]$^+$).

Example 37

4'-(N-2-Aminoethyl)aminospiro[1-azabicyclo[2.2.2]
octane-3,2'(3'H)-furo[2,3-b]pyridine]

A solution of 74 mg (0.295 mmol) of 4'-chlorospiro[1-azabicyclo[2.2.2]octane-3,2'(3'H)-furo[2,3-b]pyridine] in 10 mL of ethylenediamine was heated to reflux under a nitrogen atmosphere and stirred for 4 days. Upon cooling to ambient temperature, the solvent was removed in vacuo. The residue was dissolved in 20 mL of saturated aqueous sodium carbonate and extracted with chloroform (3×25 mL). The combined organic extract was dried over anhydrous magnesium sulfate and concentrated in vacuo to give the title compound as a dark oil, 80 mg (100%): electrospray MS (m/z, relative intensity) 275 ([MH]$^+$).

Example 38

4'-(4-N-Methylpiperazin-1-yl)spiro[1-azabicyclo
[2.2.2]octane-3,2'(3'H)-furo[2,3-b]pyridine]

A solution of 97 mg (0.387 mmol) of 4'-chlorospiro[1-azabicyclo[2.2.2]octane-3,2'(3'H)-furo[2,3-b]pyridine] in 1 mL of 1-methylpiperazine was heated to reflux under a nitrogen atmosphere and stirred for 18 hours. Upon cooling to ambient temperature, the diluted with 40 mL of water, basicified with 2 mL of saturated aqueous sodium carbonate and extracted with chloroform (3×25 mL). The combined organic extract was dried over anhydrous magnesium sulfate, concentrated in vacuo, and flash chromatographed on neutral silica gel using a 4:1 mixture of ammoniated chloroform/methanol to provide 59 mg (48%) of the title compound as an amber oil: electrospray MS (m/z, relative intensity) 315 ([MH]$^+$).

Example 39

4'-(Phenylmethyl)aminospiro[1-azabicyclo[2.2.2]
octane-3,2'(3'H)-furo[2,3-b]pyridine]

A solution of 97 mg (0.387 mmol) of 4'-chlorospiro[1-azabicyclo[2.2.2]octane-3,2'(3'H)-furo[2,3-b]pyridine] in 5 mL of benzylamine was heated to reflux under a nitrogen atmosphere and stirred for 18 hours. Upon cooling to ambient temperature, the diluted with 40 mL of water, basicified with 2 mL of saturated aqueous sodium carbonate and extracted with chloroform (3×25 mL). The combined organic extract was dried over anhydrous magnesium sulfate, concentrated in vacuo, and flash chromatographed on neutral silica gel using a 9:1 mixture of ammoniated chloroform/methanol to provide 42 mg (34%) of the title compound as a white solid: electrospray MS (m/z, relative intensity) 322 ([MH]$^+$).

Example 40

4'-(Methylamino)spiro[1-azabicyclo[2.2.2]octane-3,
2'(3'H)-furo[2,3-b]pyridine]

A solution of 151 mg (0.60 mmol) of 4'-chlorospiro[1-azabicyclo[2.2.2]octane-3,2'(3'H)-furo[2,3-b]pyridine] in 25 mL of 40% aqueous methylamine was heated to 175° C. in a steel bomb for 18 hours, then cooled to ambient temperature and concentrated in vacuo. The residue was dissolved in 10 mL of ethanol containing 0.4 mL of concentrated hydrochloric acid and the solution was allowed to stand overnight. After filtering, the solution was concentrated in vacuo and the residue crystallized from isopropanol, giving 147 mg of the title compound as a white solid: electrospray MS (m/z, relative intensity) 246 ([MH]$^+$).

Example 41

Spiro[1-azabicyclo[2.2.2]octane-3,2'(3'H)-furo[2,3-b]pyridine-7'-oxide]

A solution of spiro[1-azabicyclo[2.2.2]octane-3,2'(3'H)-furo[2,3-b]pyridine] (2.88 g, 13.3 mmol) and aqueous hydrogen peroxide (30%, 5 ml) in acetic acid (20 ml) was heated under reflux. After 16 h and 24 h, further portions of hydrogen peroxide were added, and heating was continued for a total of 48 h. The solution was then evaporated, then the residue was redissolved in ethanol (40 ml) which had been saturated with sulfur dioxide. After 4 h the solution was evaporated and the residue was purified by HPLC on silica using as the eluant a 0–50% gradient of a mixture of solvents (7 M methanolic ammonia (25%) methanol (25%) chloroform (50%)) and chloroform. The title compound (934 mg,4.0 mmol, 30%) was a solid: DCI MS 233 ([MH]$^+$).

Example 42

Spiro[1-azabicyclo[2.2.2]octane-3,2'(3'H)-furo[2,3-b]pyridine-6'-carbonitrile]

A solution of spiro[1-azabicyclo[2.2.2]octane-3,2'(3'H)-furo[2,3-b]pyridine-7'-oxide] 95 mg, 0.41 mmol) was dissolved in acetonitrile (2 ml). Triethylamine (0.12 ml, 87 mg, 0.86 mmol), and then trimethylsilyl cyanide (0.2 ml, 149 mg, 1.5 mmol) were added. The solution was stirred at room temperature overnight, then heated to reflux temperature. After approx. 8 h, further trimethylsilyl cyanide (0.2 ml) was added. After heating under reflux overnight the solution was allowed to cool. Excess methanol was added, and the solution was left at room temperature for 4 h then evaporated. The residue was purified by HPLC on silica using as the eluant a 0–25% gradient of a mixture of solvents (7 M methanolic ammonia (25%) methanol (25%) chloroform (50%)) and chloroform. The title compound (50 mg, 0.21 mmol, 51%) was a solid: electrospray MS 242 ([MH]$^+$)

Example 43

6'-Chlorospiro[1-azabicyclo[2.2.2]octane-3,2'(3'H)-furo[2,3-b]pyridine]

A solution of spiro[1-azabicyclo[2.2.2]octane-3,2'(3'H)-furo[2,3-b]pyridine-7'-oxide] (98 mg, 0.42 mmol) in phosphorous oxychloride (2 ml) was heated under reflux for 2 h. The solution was evaporated, the residue was partitioned between aqueous potassium carbonate and chloroform, then the organic layer was dried (magnesium sulfate), filtered, and evaporated. The residue was purified by HPLC on silica using as the eluant a 0–25% gradient of a mixture of solvents (7M methanolic ammonia (25%) methanol (25%) chloroform (50%)) and chloroform. The title compound (26 mg, 0.10 mmol, 25%) was a solid: electrospray MS 251 ([MH]$^+$ with $^{35}$Cl) and 253 ([MH]$^+$ with $^{37}$Cl).

Example 44

6'-Fluorospiro[1-azabicyclo[2.2.2]octane-3,2'(3'H)-furo[2,3-b]pyridine]

(a) 6'-Fluorospiro[1-azabicyclo[2.2.2]octane-3,2'
(3'H)-furo[2,3-b]pyridine]N-borane complex A solution of phenyllithium (1.8 M in cyclohexane, 13.5 mL) was added to THF (15 mL) under argon. Diisopropylamine (0.5 mL) was added, and the solution was cooled to −78° C. (dry ice/acetone bath temperature). To the resulting solution, 2,6-difluoropyridine (1.23 mL, 1.56 g, 13.6 mmol) was added dropwise, then after 1 h, a solution of spiro[1-azabicyclo[2.2.2]octane-3,2'-oxirane]N-borane complex (765 mg, 5.0 mmol) in tetrahydrofuran was added dropwise. The solution was stirred at −78° C. for 1 h and the cooling bath was then replaced with a dry ice/acetonitrile bath. The solution was then stirred overnight, warming to room temperature. Saturated aqueous sodium bicarbonate was added, and the solution was then extracted with chloroform. The extract was then dried (MgSO$_4$), filtered, and evaporated. The residue was dissolved in DMF (20 mL), and was then added to a suspension of hexane-washed sodium hydride (60% mixture with mineral oil, 507 mg, 12.7 mmol) in DMF (20 mL) stirred at 0° C. The solution was stirred overnight, warming to room temperature. Saturated aqueous sodium bicarbonate was added to the solution, which was then extracted with chloroform. The extract was then dried (MgSO$_4$), filtered, and evaporated, and the residue was purified by HPLC using a gradient of 5–50% ethyl acetate and hexane to give the sub-title compound (102 mg, 8%, 0.41 mmol): electrospray MS (m/z) 247 [M-H]$^+$.

(b) 6'-Fluorospiro[1-azabicyclo[2.2.2]octane-3,2' (3'H)-furo[2,3-b]pyridine]

6'-Fluorospiro[1-azabicyclo[2.2.2]octane-3,2'(3'H)-furo[2,3-b]pyridine]N-borane complex (98 mg, 0.40 mmol) was dissolved in acetone (5 ml). 48% Aqueous hydrobromic acid (2 ml) was diluted with water (2 ml) and then was added to the solution. The resulting mixture was stirred at room temperature overnight. The solution was then evaporated and partitioned between aqueous sodium carbonate and chloroform. The organic extract was then dried (MgSO$_4$), filtered, and evaporated, and the residue was purified by HPLC using is a gradient of 0–25% 1:1:2 7M methanolic ammonia:methanol:chloroform and chloroform to give the title compound (39 mg, 0.168 mmol, 43%) as a solid: electrospray MS (m/z, relative intensity) 235 ([MH]$^+$, 100).

What is claimed is:

1. A compound of formula I

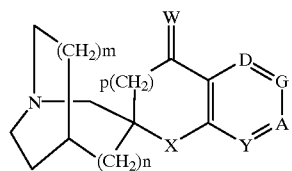

wherein n is 0 or 1;
m is 0 or 1;
p is 0 or 1;
X is oxygen or sulfur;
Y is CH, N or NO;
W is oxygen, H$_2$ or F$_2$;
A is N or C(R$^2$);
G is N or C(R$^3$);
D is N or C(R$^4$);
with the proviso that no more than one of A, G, and D is nitrogen but at least one of Y, A, G, and D is nitrogen or NO;
R$^1$ is hydrogen or C$_1$–C$_4$ alkyl;
R$^2$, R$^3$, and R$^4$ are independently hydrogen, halogen, C$_1$–C$_4$ alkyl, C$_2$–C$_4$ alkenyl, C$_2$–C$_4$ alkynyl, aryl, heteroaryl, OH, OC$_1$–C$_4$ alkyl, CO$_2$R$^1$, —CN, —NO$_2$, —NR$^5$R$^6$, —CF$_3$, —OSO$_2$CF$_3$, or R$^2$ and R$^3$, or R$^3$ and R$^4$, respectively, may together form another six membered aromatic or heteroaromatic ring sharing A and G, or G and D, respectively, containing between zero and two nitrogen atoms, and substituted with one to two of the following substituents: independently hydrogen, halogen, C$_1$–C$_4$ alkyl, C$_2$–C$_4$ alkenyl, C$_2$–C$_4$ alkynyl, aryl, heteroaryl, OH, OC$_1$–C$_4$ alkyl, CO$_2$R$^1$, —CN, —NO$_2$, —NR$^5$R$^6$, —CF$_3$, —OSO$_2$CF$_3$;

R$^5$ and R$^6$ are independently hydrogen, C$_1$–C$_4$ alkyl, C(O)R$^7$, C(O)NHR$^8$, C(O)OR$^9$, SO$_2$R$^{10}$ or may together be (CH$_2$)$_j$Q(CH$_2$)$_k$ where
Q is O, S, NR$^{11}$, or a bond;
j is 2 to 7;
k is 0 to 2;
R$^7$, R$^8$, R$^9$, R$^{10}$, and R$^{11}$ are independently C$_1$–C$_4$ alkyl, aryl, or heteroaryl,
or an enantiomer thereof, and the pharmaceutically acceptable salts thereof.

2. A compound according to claim 1 wherein m is 1.
3. A compound according to claim 1 wherein n is 0.
4. A compound according to claim 1 wherein p is 0.
5. A compound according to claim 1 wherein X is oxygen.
6. A compound according to claim 1 wherein A is C(R$^2$); G is C(R$^3$); and D is C(R$^4$).
7. A compound according to claim 1 wherein m is 1; n is 0; p is 0; X is oxygen; A is C(R$^2$); G is C(R$^3$); D is C(R$^4$).
8. A compound according to claim 1, said compound being:

spiro[1-azabicyclo[2.2.2]octane-3,2'-(3'H)-furo[2,3-b]pyrdine];
5'-bromospiro[1-azabicyclo[2.2.2]octane-3,2'-(3'H)-furo[2,3-b]pyridine];
5'-phenylspiro[1-azabicyclo[2.2.2]octane-3,2'-(3'H)-furo[2,3-b]pyridine];
5'-nitrospiro[1-azabicyclo[2.2.2]octane-3,2'-(3'H)-furo[2,3-b]pyridine];
1'-chlorospiro[1-azabicyclo[2.2.2]octane-3,2'-(3'H)-furo[2,3-b]isoquinoline];
5'-(phenylcarboxamido)spiro[1-azabicyclo[2.2.2]octane-3,2'-(3'H)-furo[2,3-b]pyridine];
5'-(phenylaminocarbonylamino)spiro[1-azabicyclo[2.2.2]octane-3,2'-(3'H)-furo[2,3-b]pyridine];
5'-(phenylsulfonylamido)spiro[1-azabicyclo[2.2.2]octane-3,2'-(3'H)-furo[2,3-b]pyridine];
5'-aminospiro[1-azabicyclo[2.2.2]octane-3,2'-(3'H)-furo[2,3-b]pyridine];
5'-N-methylaminospiro[1-azabicyclo[2.2.2]octane-3,2'-(3'H)-furo[2,3-b]pyridine];
5'-N,N-dimethylaminospiro[1-azabicyclo[2.2.2]octane-3,2'-(3'H)-furo[2,3-b]pyridine]; 5'-N,N-diethylaminospiro[1-azabicyclo[2.2.2]octane-3,2'-(3'H)-furo[2,3-b]pyridine];
5'-N-ethylaminospiro[1-azabicyclo[2.2.2]octane-3,2'-(3'H)-furo[2,3-b]pyridine];
5'-N-benzylaminospiro[1-azabicyclo[2.2.2]octane-3,2'-(3'H)-furo[2,3-b]pyridine];
5'-N-formamidospiro[1-azabicyclo[2.2.2]octane-3,2'-(3'H)-furo[2,3-b]pyridine];
5'-N-acetamidospiro[1-azabicyclo[2.2.2]octane-3,2'-(3'H)-furo[2,3-b]pyridine];
spiro[1-azabicyclo[2.2.2]octane-3,2'-(3'H)-furo[2,3-b]isoquinoline];
spiro[1-azabicyclo[2.2.2]octane-3,2'-(3'H)-furo[2,3-b]quinoline];
5'-ethenylspiro[1-azabicyclo[2.2.2]octane-3,2'-(3'H)-furo[2,3-b]pyridine];

5'-(E)-(phenylethenyl)spiro[1-azabicyclo[2.2.2]octane-3,2'-(3'H)-furo[2,3-b]pyridine];
5'-(4-morpholino)spiro[1-azabicyclo[2.2.2]octane-3,2'-(3'H)-furo[2,3-b]pyridine];
5'-(1-azetidinyl)spiro[1-azabicyclo[2.2.2]octane-3,2'-(3'H)-furo[2,3-b]pyridine];
5'-(E)-(2-(4-pyridyl)ethenyl)spiro[1-azabicyclo[2.2.2]octane-3,2'-(3'H)-furo[2,3-b]pyridine];
5'-(E)-(2-(2-pyridyl)ethenyl)spiro[1-azabicyclo[2.2.2]octane-3,2'-(3'H)-furo[2,3-b]pyridine];
5'-(2-trimethylsilylethynyl(spiro[1-azabicyclo[2.2.2]octane-3,2'-(3'H)-furo[2,3-b]pyridine];
5'-ethynylspiro[1-azabicyclo[2.2.2]octane-3,2'-(3'H)-furo[2,3-b]pyridine];
5'-(2-furyl)spiro[1-azabicyclo[2.2.2]octane-3,2'-(3'H)-furo[2,3-b]pyridine];
5'-(3-pyridyl)spiro[1-azabicyclo[2.2.2]octane-3,2'-(3'H)-furo[2,3-b]pyridine];
5'-methylspiro[1-azabicyclo[2.2.2]octane-3,2'-(3'H)-furo[2,3-b]pyridine];
spiro[1-azabicyclo[2.2.2]octane-3,2'-3'H)-furo[2,3-b]pyridine-5'carbonitrile];
spiro[1-azabicyclo[2.2.2]octane-3,2'-(3'H)-furo[2,3-b]pyridine-5'carboxamide];
5'-N'-(3chlorophenyl)ureidoaminospiro[1-azabicyclo[2.2.2]octane-3,2'-(3'H)-furo[2,3-b]pyridine];
5'-N'-(2-nitrophenyl)ureidoaminospiro[1-azabicyclo[2.2.2]octane-3,2'-(3'H)-furo[2,3-b]pyridine];
4'chlorospiro[1-azabicyclo[2.2.2]octane-3,2'-(3'H)-furo[2,3-b]pyridine];
4'-methoxyspiro[1-azabicyclo[2.2.2]octane-3,2'-(3'H)-furo[2,3-b]pyridine];
4'-phenylthiospiro[1-azabicyclo[2.2.2]octane-3,2'-(3'H)-furo[2,3-b]pyridine];
4'-(N-2-aminoethyl)aminospiro[1-azabicyclo[2.2.2]octane-3,2'-(3'H)-furo[2,3-b]pyridine];
4'-Phenylaminospiro[1-azabicyclo[2.2.2]octane-3,2'-(3'H)-furo[2,3-b]pyridine];
4'-methylaminospiro[1-azabicyclo[2.2.2]octane-3,2'-(3'H)-furo[2,3-b]pyridine];
4'-(4-N-methylpiperazin-1-yl)spiro[1-azabicyclo[2.2.2]octane-3,2'-(3'H)-furo[2,3-b]pyridine];
4'-chloro-spiro[1-azabicyclo[2.2.2]octane-3,2'-(3'H)-furo[3,2-c]pyridine];
spiro[1-azabicyclo[2.2.2]octane-3,2'-(3'H)-furo[3,2-c]pyridine];
6'-fluorospiro[1-azabicyclo[2.2.2]octane-3,2'(3'H)-furo[2,3-b]pyridine];
spiro[1-azabicyclo[2.2.2]octane-3,2'(3'H)-furo[2,3-b]pyridine-6'-carbonitrile];
6'-chlorospiro[1-azabicyclo[2.2.2]octane-3,2'(3'H)-furo[2,3-b]pyridine];

or an enantiomer, or a pharmaceutically acceptable salt thereof.

9. A compound according to claim 1 in which Y is NO.

10. A compound according to claim 9, being spiro[1-azabicyclo[2.2.2]octane-3,2'(3'H)-furo[2,3-b]pyridine-7'-oxide]; or a pharmaceutically acceptable salt, or an enantiomer, thereof.

11. A pharmaceutical composition including a compound as defined in claim 1, in admixture with an inert pharmaceutically acceptable diluent or carrier.

12. A method of treatment or prophylaxis of human diseases or conditions in which activation of the α7 nicotinic receptor is beneficial which comprises administering a therapeutically effective amount of a compound as defined in claim 1.

13. A method of treatment or prophylaxis of psychotic disorders or intellectual impairment disorders, which comprises administering a therapeutically effective amount of a compound as defined in claim 1.

14. The method as claimed in claim 13, wherein the disorder is Alzheimer's disease, learning deficit, cognition deficit, attention deficit, memory loss, or Attention Deficit Hyperactivity Disorder.

15. The method as claimed in claim 13, wherein the disorder is Parkinson's disease, Huntington's disease, Tourette's syndrome, or neurodegenerative disorders in which there is loss of cholinergic synapses.

16. The method as claimed in claim 13, wherein the disorder is anxiety, schizophrenia or mania or manic depression.

17. A method of treatment or prophylaxis of jetlag, cessation of smoking, nicotine addiction, pain, and for ulcerative colitis which comprises administering a therapeutically effective amount of a compound as defined in claim 1.

18. A process for preparation of a compound of formula I, as defined in claim 1, wherein Y is N, or an enantiomer thereof, or a pharmaceutically acceptable salt, which comprises:

removal of a borane complex in a compound of formula II using acid in a suitable solvent or heating the complex in an alcoholic solvent

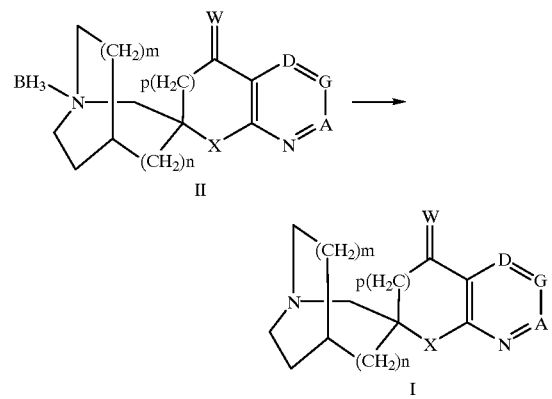

and when W=$F_2$ allowed by reaction with diethylaminosulfur trifluoride, and where desired or necessary converting the resultant compound of formula I, or enantiomer thereof or an acid addition salt thereof, to a pharmaceutically acceptable acid addition salt thereof, or converting the resultant racemic mixture of the compound of formula I to an enantiomer thereof.

19. A process for the preparation of a compound of the formula I as defined in claim 1 wherein $R^1$ is hydroxyl and Y is N, by rearrangement of a compound of the formula I as defined in claim 1, wherein Y is NO, by reacting with a carboxylic anhydride in a suitable solvent.

20. A process for the preparation of a compound of the formula I as defined in claim 1 wherein $R^1$ is chloro and Y is N, by rearrangement of a compound of the formula I as defined in claim 1, wherein Y is NO, by reacting with a chlorinating source in a suitable solvent.

21. A process for the preparation of a compound of the formula I as defined in claim 1 wherein $R^1$ is cyano and Y is N, by rearrangement of a compound of the formula I as defined in claim 1, wherein Y is NO, by reacting with a source of cyanide in a suitable solvent.

22. A process for the preparation of a compound of formula I as defined in claim 20 wherein said chlorinating source is phosphorous oxychloride.

23. A process for the preparation of a compound of the formula I as defined in claim 21 wherein said source of cyanide is trimethylsilyl cyanide.

* * * * *